United States Patent [19]

Yoshida et al.

[11] 4,169,109

[45] Sep. 25, 1979

[54] PROCESS FOR PREPARING KETONES USING ZINC ACETATE CONDENSATION CATALYSTS, PRODUCTS PRODUCED THEREBY AND ORGANOLEPTIC USES OF SAME

[75] Inventors: Takao Yoshida, West Long Branch; John B. Hall, Rumson, both of N.J.

[73] Assignee: International Flavors & Fragrances Inc., New York, N.Y.

[21] Appl. No.: 932,649

[22] Filed: Aug. 10, 1978

[51] Int. Cl.$^2$ ............................................... C07C 45/00
[52] U.S. Cl. ........................... 260/586 C; 260/590 E; 260/592; 260/593 R
[58] Field of Search ............... 260/586 C, 590 E, 592, 260/593 R

[56] References Cited

U.S. PATENT DOCUMENTS

| | | | |
|---|---|---|---|
| 2,357,260 | 8/1944 | Joyce | 260/586 C |
| 2,393,510 | 1/1946 | Bailey et al. | 260/586 C |
| 2,549,508 | 4/1951 | Mottern | 260/593 R |
| 3,248,428 | 4/1966 | Porter et al. | 260/593 R |
| 3,980,716 | 9/1976 | Elliott | 260/586 C |
| 4,005,147 | 1/1977 | Fischer et al. | 260/593 R |
| 4,086,188 | 4/1978 | Reichle | 260/586 C |

FOREIGN PATENT DOCUMENTS 1203243 10/1965 Fed. Rep. of Germany .

OTHER PUBLICATIONS

"Organic Reactions", vol. 16, pp. 27–47, 69–78, 88, 115 and 177–et seq. (1968), John Wiley and Sons.

*Primary Examiner*—Norman Morgenstern
*Attorney, Agent, or Firm*—Arthur L. Liberman; Franklin D. Wolffe

[57] ABSTRACT

Described is a process for the production of alpha, beta unsaturated ketones by reaction of an aldehyde with a ketone in the presence of a catalyst consisting essentially of either zinc acetate or zinc acetate dihydrate. The ketones obtained are suitable and some cases as solvents and in some cases as intermediates for the production of valuable odorants, dyes, plastics and especially nature-identical substances and are also useful as odorants per se.

4 Claims, 18 Drawing Figures

GLC PROFILE FOR EXAMPLE IV.

NMR SPECTRUM FOR EXAMPLE IV, FRACTION 8.

SOLVENT: CDCl₃
SWEEP WIDTH: 1000 Hz.

GLC PROFILE FOR EXAMPLE V

GLC PROFILE FOR EXAMPLE VII.

IR SPECTRUM FOR EXAMPLE IX, PEAK B.

GLC PROFILE FOR EXAMPLE X

GLC PROFILE FOR EXAMPLE XII.

GLC PROFILE FOR EXAMPLE XIII.

GLC PROFILE FOR EXAMPLE XIV

GLC PROFILE FOR EXAMPLE XV, RUN 10

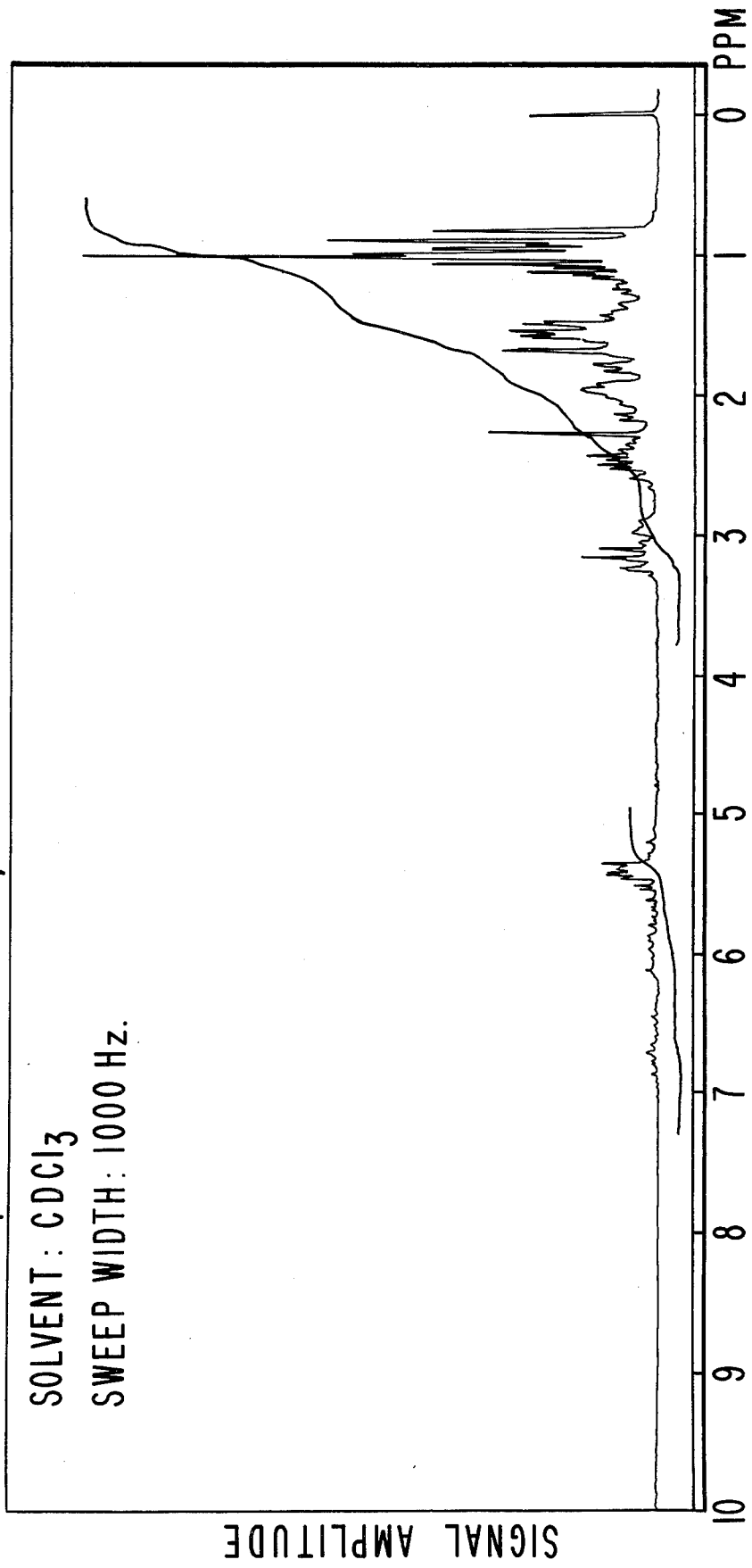

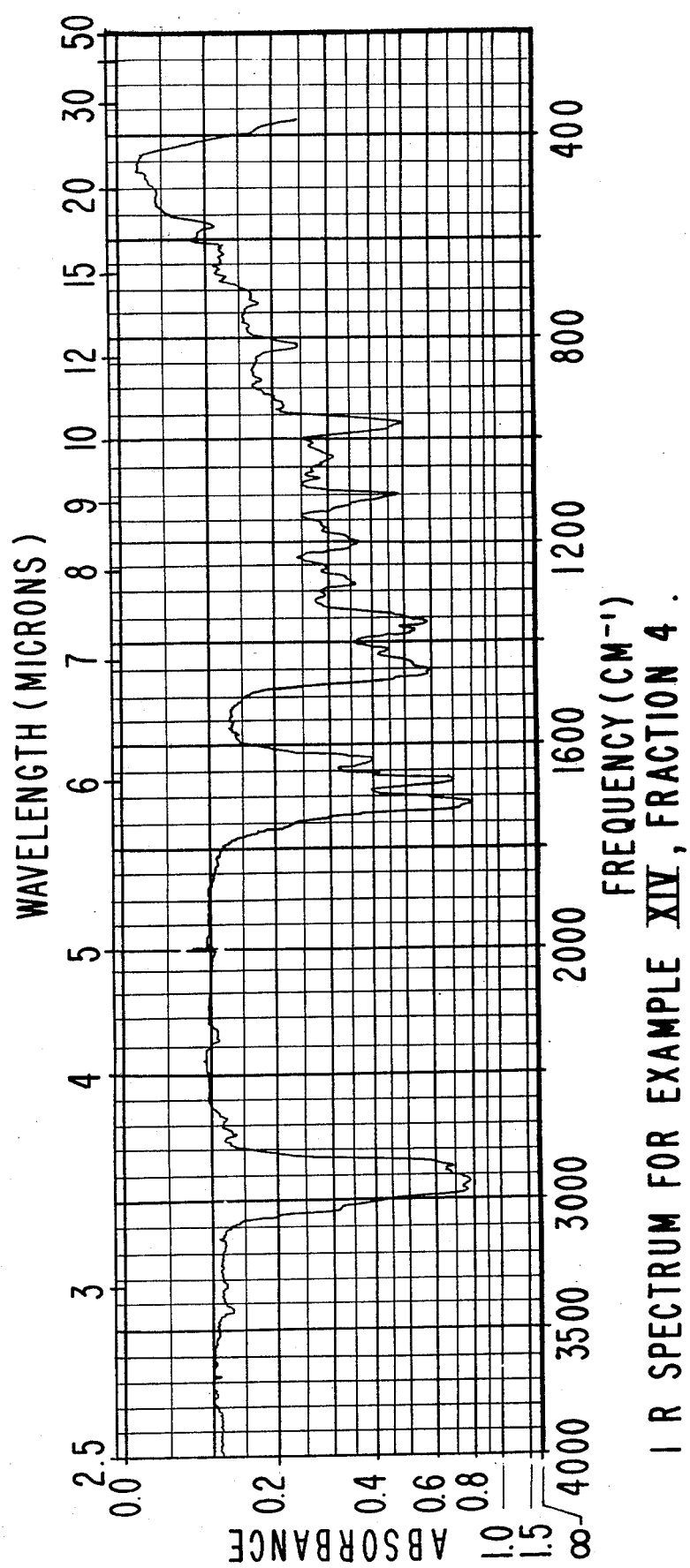
FIG.15 IR SPECTRUM FOR EXAMPLE XIV, FRACTION 4.

NMR SPECTRUM FOR EXAMPLE XV, RUN 10.

IR SPECTRUM FOR EXAMPLE XV, RUN 10.

PROCESS FOR PREPARING KETONES USING ZINC ACETATE CONDENSATION CATALYSTS, PRODUCTS PRODUCED THEREBY AND ORGANOLEPTIC USES OF SAME

BACKGROUND OF THE INVENTION

The invention relates to a process for the production of ketones unsaturated in the alpha, beta position to the carbonyl group by reacting an aldehyde with a ketone in the presence of a catalyst consisting essentially of either of zinc acetate or zinc acetate dihydrate.

On even date herewith U.S. application for Letters Patent Nos., entitled: "2,2,3-trimethyl-3-cyclopenten-1-ylalkenyl and alkylidene secondary alkanols, alkanones, cycloalkanols and cycloalkanones, organoleptic uses thereof in perfume compositions, colognes and perfumed articles and process for producing same", discloses and claims a process using a zinc acetate catalyst or a zinc acetate dihydroate catalyst to provide a highly efficient, advantageous unobvious rout to produce a number of compounds including certain novel compounds heretofore unavailable having the generic structure:

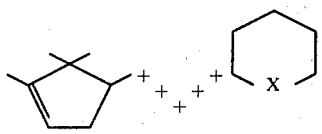

wherein in one of the lines + + + + is a carbon-carbon single bond and the other of the lines + + + + is a carbon-carbon double bond and wherein X is one of the moieties

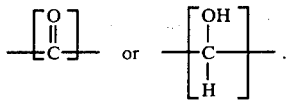

The use of zinc acetate in carrying out such reactions has heretofore been unknown and is not obvious from the teachings of the prior art. Thus, Houben-Weyl, "Methoden der Organischen Chemie", volume 7/1, pages 77 et seq. and "Organic Reactions", volume 16, pages 27 to 47, 69 to 78 and 177 et seq. disclose the fact that aldehydes and ketones can be converted to alpha, beta unsaturated ketones. Temperatures of from 5° C. up to 100° C. are preferred for this aldol condensation ("Organic Reactions," loc. cit., page 77). The numerous catalysts used in these methods, for example alkali and alkaline earth metal hydroxides, organic bases, alkali metal salts and alcoholates promote auto-condensation of the aldehydes and ketones and therefore cause the formation of large amounts of by-products in most cases.

Furthermore, the U.S. Pat. No. 4,005,147 discloses the production of alpha, beta unsaturated ketones by reacting in the liquid phase an aldehyde with a ketone in the presence of a catalyst consisting essentially of zinc oxide.

It is furthermore known from U.S. Pat. No. 2,549,508 that aldehydes and ketones can be converted into unsaturated ketones of high molecular weight in the gas phase at temperatures of from 500° to 1000° C. in the presence of a catalyst consisting essentially of zinc oxide and from 1 to 15% by weight of zirconium oxide. In this process, however, only low conversions and low yields are achieved. Moreover high expenditure for equipment is required for reactions in the presence of hydrogen at the said temperatures for safety reasons. Moreover cracking processes take place at the surface of the catalyst in such reactions and these have a negative effect on the life of the catalyst.

The reaction of two identical or different aldehydes or ketones in the liquid phase at elevated temperature and in the presence of a catalyst (obtained by calcining a mixture of molybdenum oxide, magnesium oxide with or without zinc oxide or compounds of these metals) to form alpha, beta-unsaturated aldehydes or ketones is known from German Pat. No. 1,203,243.

According to the method described in the said patent good conversions and very good yields of alpha, beta-unsaturated aldehydes are obtained in the condensation of aldehydes with one another, particularly in the condensation of n-butyraldehyde or 2-ethylhexenal.

The process of German Pat. No. 1,203,243 is not so suitable for the reaction of aldehydes with ketones to form alpha, beta-unsaturated ketones, considerably lower conversions and selectivities being achieved. This is particularly noticeable when not only isobutyraldehyde (i.e., and aldehyde which does not undergo autocondensation) is reacted with a ketone by the method of the said German patent, but also when aldehydes are used which readily undergo autocondensation, as for example 3,3-dimethylacrolein and citral.

Nothing in the prior art however implies the process of our invention using either a zinc acetate catalyst or a zinc acetate dihydrate catalyst whereby certain ketones may be produced in a convenient, sufficient and economical manner.

BRIEF DESCRIPTION OF THE DRAWINGS

FIG. 14 is the NMR spectrum for 5-(2,6,6-trimethyl-1(and 2)-cyclohexene-1-yl)-3-methyl-3-penten-2-one, fraction 4 produced according to Example XIV.

FIG. 15 is the IR spectrum for 5-(2,6,6-trimethyl-1(and 2)-cyclohexene-1-yl)-3-methyl-3-penten-2-one, fraction 4 produced according to Example XIV.

THE INVENTION

Figure 1:
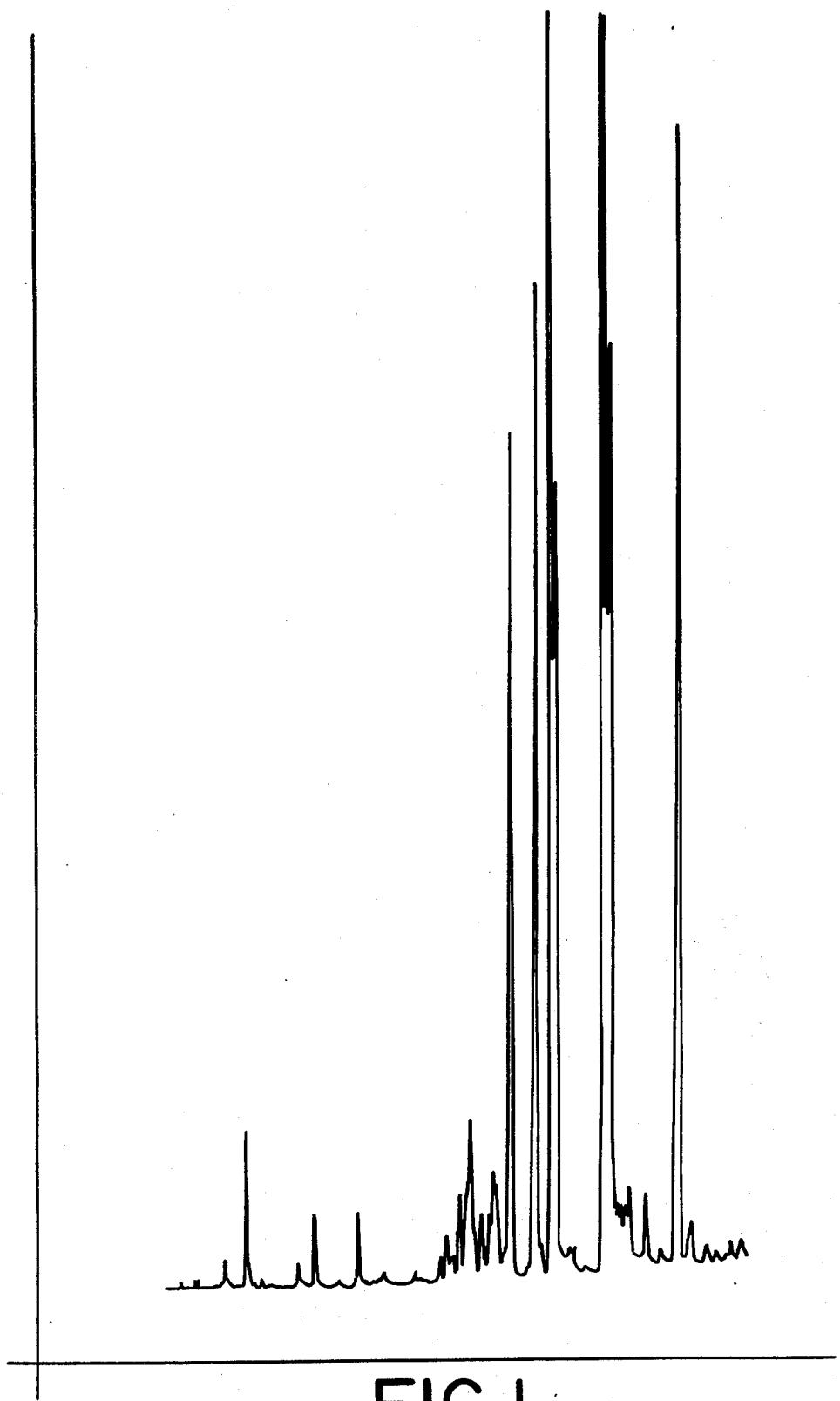
FIG. 1 is the GLC profile for 5-methyl-3,5-octadien-2-one produced according to Example IV.

This invention covers a process which enables aldehydes, particularly aldehydes having a tendency for autocondensation to be reacted selectively with ketones to alpha, beta unsaturated ketones with good conversions and excellent yields.

More specifically our invention covers the following reaction schemes:

Scheme "A"

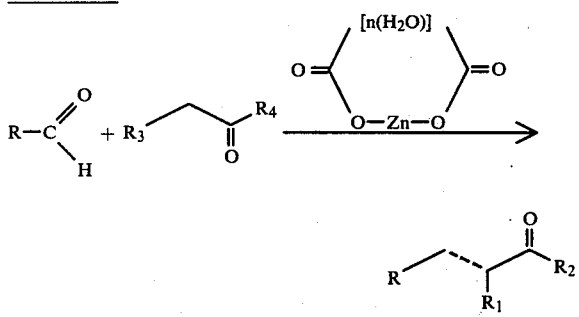

wherein the dashed line represents a cis or trans carbon-carbon double bond and n=0 or 2

Scheme "B"

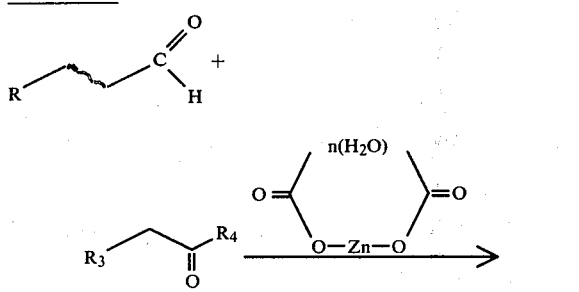

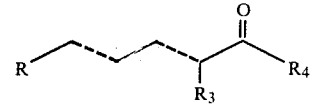

wherein the wavy line and each of the dashed lines represent cis or trans carbon-carbon double bonds and n=0 or 2; and wherein R is lower alkyl having from one up to about five carbon atoms; aralkyl having seven or eight carbon atoms; alkenyl having from three up to twelve carbon atoms; alkadienyl having from eight up to twelve carbon atoms; alkyl cycloalkenyl alkyl having from eight up to ten carbon atoms; alkyl alkenyl having from seven up to nine carbon atoms and aralkyl having seven or eight carbon atoms; wherein $R_1$ and $R_3$ are each the same or different and each represents hydrogen or lower alkyl having from one up to five carbon atoms; and wherein $R_2$ and $R_4$ are each the same or different and each represents lower alkyl having from one up to five carbon atoms.

The use of zinc acetate and zinc acetate dihydrate gives rise to unexpected, unobvious and advantageous results and also gives rise to novel compounds heretofore not made particularly in view of their apparent difficulty of manufacture.

In the above stated reaction schemes the mole ratio of catalyst:ketone reactant may vary from about 0.05:1 up to about 1:1 with a preferable mole ratio of catalyst:ketone reactant being about 0.2:1.

In the above mentioned reaction sequences the mole ratio of ketone:aldehyde reactants may vary from about 1:1 up to about 10:1 with a preferable mole ratio of ketone:aldehyde reactant being from about 3 up to about 5.

In each of the above mentioned reaction sequences the temperature may vary from about 100° C. up to about 250° C. with a preferable reaction temperature being in the range of from 130° C. up to 200° C.

Although the above mentioned reactions may be carried out at atmospheric pressure it is preferred to carry out these reactions in equipment which can withstand higher pressures; particularly a pressure buildup of the order of from about 100 up to about 400 psig.

Previously mentioned bases such as sodium hydroxide or potassium hydroxide and zinc oxide (100% pure) were used for catalysis of aldol condensations whereby undesired self condensation products were produced (such as mesityl oxide in the case of acetone which is difficult to remove from the product of reaction, in the case of, for example, 3-penten-2-one). According to our invention a minimal quantity of self condensation product results.

More specifically in the case of the reaction involving acetaldehyde and methyl ethyl ketone reactants using a zinc oxide catalyst the product ratio of 4-hexen-3-one to 3-methyl-3-penten-2-one is 6.3:37 with a yield of about 13%. Whereas U.S. Pat. No. 4,005,147 teaches the requirement of application of high pressures to the reaction mass, our invention does not require such immediate application of pressure to the reaction mass although it is generally convenient to carry out the reaction in vessels that can withstand pressures of from about 100 up to about 400 psig.

The following table is a summary of the specific examples carried out and illustrated infra.

TABLE I

| Example | Ketone Reactant | Aldehyde Reactant | Reaction Temperature | Reaction Time | Main Constituent(s) Of Reaction Product | Yield (%) |
|---|---|---|---|---|---|---|
| I, II, XV | acetone | acetaldehyde (H₃C-CHO) | 140° C. | 3 Hours | (E and Z isomers of methyl propenyl ketone) | 43 |
| V | methyl ethyl ketone | acetaldehyde (H₃C-CHO) | 130°–140° C. | 6 Hours | (mixture of four unsaturated ketones) | 38 |
| XIII | methyl ethyl ketone | propanal | 190° C. | 12 Hours | Mixture wherein in each molecule one of the dashed lines is a carbon-carbon single bond and, the other of the dashed lines is a cis or trans carbon-carbon double bond. | 35 |
| VI | acetone | citronellal-type aldehyde | 150° C. | 3 Hours | Wherein one of the dashed lines is a carbon-carbon single bond and the other of the dashed lines is a cis or trans carbon-carbon double bond | 12 |
| VII | methyl ethyl ketone | citronellal-type aldehyde | 160° C. | 8 Hours | Wherein one of the dashed lines is a carbon-carbon single bond and the other of the dashed lines is a cis or trans carbon-carbon double bond. | 45 |
| VIII | methyl isobutyl ketone | citronellal-type aldehyde | 160° C. | 8 Hours | (two unsaturated ketones) | 32 |
| IX | acetone | 4-methyl-3-cyclohexene-1-carboxaldehyde | 180° C. | 7 Hours | Wherein one of the dashed lines is a carbon-carbon single bond and the other of the dashed lines is a cis or trans carbon-carbon double bond. | 47 |

TABLE I-continued

| Example | Ketone Reactant | Aldehyde Reactant | Reaction Temperature | Time | Main Constituent(s) Of Reaction Product | Yield (%) |
|---|---|---|---|---|---|---|
| X | [methyl ethyl ketone] | [4-methyl-3-cyclohexene-1-carboxaldehyde] | 150° C. | 10 Hours | [mixture of two products] Wherein one of the dashed lines is a carbon-carbon single bond and the other of the dashed lines is a cis or trans carbon-carbon double bond. | 57 |
| XIV | [methyl ethyl ketone] | [trimethyl cyclohexene acetaldehyde] | 190° C. | 8 Hours | [mixture of two products] (Mixture of compounds wherein one of the dashed lines is a cis or trans carbon-carbon double bond and the other of the dashed lines is a carbon-carbon single bond; and wherein one of the wavy lines is a carbon-carbon single bond and the other of the wavy lines is a carbon-carbon double bond. | 56 |
| XI | [acetone] | [2-phenylpropanal] | 150°–165° C. | 10 Hours | [product] Wherein one of the dashed lines is a carbon-carbon single bond and the other of the dashed lines is a cis or trans carbon-carbon double bond. | 54 |
| XII | [methyl ethyl ketone] | [2-phenylpropanal] | 150°–170° C. | 10 Hours | [mixture of two products] Wherein one of the dashed lines is a carbon-carbon single bond and the other of the dashed lines is a cis or trans carbon-carbon double bond. | 59 |
| III | [acetone] | [crotonaldehyde + cis-crotonaldehyde] | 135° C. | 3.5 Hours | [product] Mixture wherein the dashed lines represent cis or trans carbon-carbon double bond. | 34 |
| IV | [acetone] | [mixture of methyl pentenals] | 170°–180° C. | 5 Hours | [product] Mixture wherein each of the dashed lines represents cis or trans carbon-carbon double bonds. | 34 |

Examples of three of the reaction products prepared herein which are useful particularly for their organoleptic properties are set forth in the following Table II:

| NAME & STRUCTURE OF MATERIAL | PERFUME PROPERTIES | FOOD FLAVOR PROPERTIES | TOBACCO FLAVOR PROPERTIES |
|---|---|---|---|
| 5-Methyl-3,5-octa-dien-2-one 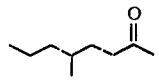 (Mixture wherein each of the dashed lines represents cis or trans carbon-carbon double bond.) | At 10% in Food Grade Alcohol a powerful, spicy, nutty, (walnut) aroma with a fruity (citrusy, melony) character. | Sweet, nutty, woody, cinnamon like aroma with a sweet, nutty, woody, cinnamon, nut meat-like char- at 3ppm; useful in cinnamon and nut meat-flavor food-stuffs. | |
| 3-Methyl-5-(2,6,6-trimethyl-1(and 2)-cyclohexen-1-yl)-3 (and 4)-penten-2-one 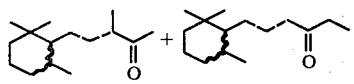 (Mixture of compounds wherein one of the dashed lines is a cis or trans carbon-carbon double bond and the other of the dashed lines is a carbon-carbon single bond; and wherein one of the wavy lines is a carbon-carbon single bond and the other of the wavy lines is a carbon-carbon double bond.) | A buttery, woody-ionone like aroma with a sour berry nuance. | A floral/ionone aroma character and floral/ionone flavor character at 2ppm. | |
| 4-(4-Methyl-3-cyclohexene-1-yl)-3-buten-2-one 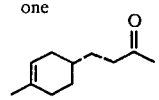 Mixture of comps. wherein one of the dashed lines is a carbon-carbon single bond and the other of the dashed lines is a cis or trans carbon-carbon double bond.) | At 10% in Food Grade Ethanol the cis isomer has a green, herbaceous, melony nuance; the trans isomer has a sweet, fatty, green spicy aroma; together the cis & trans isomer mixture has a green, herbaceous spicy, melony aroma with a woody undertone. | The mixture of cis and trans isomers at 0.2ppm has a green, floral, sandalwood-like, geranium like, spicy and citrusy aroma characteristic with a green, floral, sandalwoody-like, geranium, spicy and citrusy flavor characteristic. | |

When the ketones of our invention are used as food flavor adjuvants the nature of the co-ingredients included with the ketones used in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible, non-toxic materials which have medicinal value such as cough syrups, cough drops, aspirin and chewable medicial tablets.

The term "chewing gum" is intended to mean a composition which comprises a substantially water insoluble, chewable plastic gum base such as chicle or substitutes therefor including jelutong, guttakay, rubber or certain comestible natural or synthetic resins or waxes. Incorporated with the gum base in admixing therewith may be plasticizers or softening agents, e.g., glycerine; and a flavoring composition which incorporates one or more of the ketones made according to the process of our invention, and in addition, sweetening agents which may be sugars, ncluding sucrose or dextrose and/or artificial sweeteners such as cyclamates, saccharin or dihydrochalcones. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unaccpetable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials, lipids; carbohydrates; starches, pectins and emulsifiers, e.g., mono- and diglycerides of fatty acids, skim milk powder, hexoses, pentoses, disaccharides, e.g., sucrose corn syrup and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caprioc acid, caprylic acid, cinnamic acid, isobutyric acid, isovaleric acid, alpha-methyl-butyric acid, propionic acid, valeric acid, 2-methyl-2-pentenoic acid and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethylacrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methulphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the ketone(s) produced according to the process of our invention by not covering or spoiling the organoleptic properties (aroma and/or taste) thereof; (ii) be non-reactive with the ketone(s) produced according to the process of our invention and (iii) be capable of providing an environment in which the ketone(s) produced according to the process of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of sold products, e.g., simulated foodstuffs, ingredients capable of providing normally solid compositions should be selected such as various cellulose derivatives.

As will be appreciated by those skilled in the art, the amount of the ketone(s) produced according to the process of our invention employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the ketone(s) produced according to the process of our invention will, of course, substantially vitiate any possibility of obtaining the desired results while excess quantities prove needlessly costly and in extreme cases, may disrup the flavor-aroma balance, thus proving self-defeating. Accordingly, the terminology "effective amount" and "sufficient amount" is to be accorded a significance in the context of the present invnetion consistent with the obtention of desired flavoring effects.

Thus, and with respect to ultimate food compositions, chewing gum compositions, medicinal product compositions and toothpaste compositions, it is found that quantities of the ketone(s) produced according to the process of our invention ranging from a small but effective amount, e.g., 0.02 parts per million up to about 100 parts per million based on total composition are suitable. Concentrations in excess of the maximum quantity stated are not normally recommended, since they fail to prove commensurate enhancement of organoleptic properties. In those instances, wherein the ketone(s) produced according to the process of our invention is added to the foodstuff as an integral component of a flavoring composition, it is, of course, essential that the total quantity of flavoring composition employed be sufficient to yield an effective concentration of the ketone(s) produced according to the process of our invention in the foodstuff product.

Food flavoring compositions prepared in accordance with the present invention preferably contain the ketone(s) produced according to the process of our invention in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the compound ketone(s) produced according to the process of our invention with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the ketone(s) produced according to the process of our invention in a dry blender until the requisite degree of uniformity is achieved.

It is presently preferred to combine with the ketone(s) produced according to the process of our invention the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl Anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamm-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2-pentenal;
3-Phenyl-4-pentenal diethyl acetal;
beta-Damascone (1-crotonyl-2,6,6-trimethylcyclohex-1-ene;
beta-Damascenone (1-crotonyl-2,6,6-trimethylcyclohex-1-ene carboxaldehyde);
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl) norbornadiene prepared according to U.S. Pat. No. 3,886,289, issued on May 27, 1975.

The ketone(s) produced according to the process of our invention and one or more auxiliary perfume ingredients, including for example, alcohols, aldehydes, ketones other than the ketone(s) produced according to the process of our invention, terpinic hydrocarbons, nitriles, esters, lactones, natural essential oils and synthetic essential oil, may be admixed so that the combined odors of the individual components produce a pleasant and desired fragrance, particularly and preferably in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, the ketone(s) produced according to the process of our invention can be used to alter, modify or enhance the aroma characteristics of a perfume composition, for example, by utilizing or moderating the olfactory reaction contributed by another ingredient in the composition.

The amount of the ketone(s) produced according to the process of our invention which will be effective in perfume compositions as well as in perfumed articles and colognes depends on many factors, including the other ingredients, their amounts and the effects which are desired. It has been found that perfume compositions containing as little as 0.01% of the ketone(s) produced according to the process of our invention or even less (e.g. 0.005%) can be used to impart a spicy, nutty, citrusy and/or sandalwood aromas to soaps, cosmetics or other products. The amount employed can range up to 70% of the fragrance components and will depend on considerations of cost, nature of the end product, the effect desired on the finished product and the particular fragrance sought.

The ketone(s) produced according to the process of our invention is useful (taken alone or together with the other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and the like. When used as (an) olfactory component(s) as little as 0.1% of the ketone(s) produced according to the process of our invention will suffice to impart intense spicy, nutty, citrusy and/or sandalwood notes to woody formulations. Generally, no more than 3% of the ketone(s) produced according to the process of our invention, based on the ultimate end product, is required in the perfume composition.

In addition, the perfume composition or fragrance composition of our invention can contain a vehicle, or carrier for the ketone(s) produced according to the process of our invention. The vehicle can be a liquid such as a non-toxic alcohol, a non-toxic glycol, or the like. The carrier can also be an absorbent solid, such as a gum (e.g., gum arabic) or components for encapsulating the composition (such as gelatin).

It will thus be apparent that the ketone(s) prepared according to the process of our invention can be utilized to alter, modify or enhance sensory properties, particularly organoleptic properties, such as flavor(s) and/or fragance(s) of a wide variety of consumable materials.

Furthermore, the ketone(s) produced according to the process of our invention are capable of supplying and/or potentiating certain flavor and aroma notes usually lacking in many tobacco flavors heretofore provided.

As used herein in regard to tobacco flavors, the terms "alter" and "modify" in their various forms mean "supplying or imparting flavor character or note to otherwise bland tobacco, tobacco substitutes, or tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of tobacco or a tobacco substitute or a tobacco flavor.

Our invention thus provides an organoleptically improved smoking tobacco product and additives therefor, as well as methods of making the same which overcome specific problems heretofore encountered in which specific desired Virginia-type tobacco aroma and taste nuances thereof, are created or enhanced and may be readily controlled and maintained at the desired uniform level regardless of variations in the tobacco components of the blend.

This invention further provides improved tobacco additives and methods whereby various Virginia-type tobacco notes may be imparted to smoking tobacco products and may be readily varied and controlled to product the desired uniform flavor characteristics.

In carrying out this aspect of our invention, we add to smoking tobacco materials or a suitable substitute therefor (e.g., dried lettuce leaves) an aroma and flavor additive containing as an active ingredient a ketone(s) produced according to the process of our invention.

In addition to the ketone(s) produced according to the process of our invention, other flavoring and aroma additives may be added to the smoking tobacco materials or substitute therefor either separately or in mixture with the ketone(s) produced according to the process of our invention as follows:

(i) Synthetic Materials:

Beta-ethyl-cinnamaldehyde;
Beta-cyclohomocitral;
Eugenol;
Dipentene;
Beta-Damascenone;
Beta-Damascone;
Maltol;
Ethyl Maltol;
Delta-undecalactone;
Delat-decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho[2,1,b]-furan;

4-Hydroxy hexanoic acid, gamma lactone; and Polyisoprenoid hydrocarbons defined in Example V of U.S. Pat. No. 3,589,372, issued on June 29, 1971.

(ii) Natural Oils:

Celery seed oil;
Coffee extract;
Bergamot Oil;
Cocoa extract;
Nutmeg Oil;
Origanum Oil.

An aroma and flavoring concentrate containing ketone(s) produced according to the process of our invention and, if desired, one or more of the above-indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of the ketone(s) produced according to the process of our invention to smoking tobacco material is between 250 ppm and 1,500 ppm (0.025%–0.15%) of the active ingredients to the smoking tobacco material. We have further found that satisfactory results are obtained if the proportion by weight of the sum total of the ketone(s) produced according to the process of our invention used to flavoring material is between 2,500 and 15,000 ppm (0.25%–1.5%).

Any convenient method for incorporating the ketone(s) produced according to the process of our invention in the tobacco product may be employed. Thus, the ketone(s) produced according to the process of our invention taken alone or along with other flavoring additives may be dissolved in a suitable solvent such as ethanol, pentane, diethyl ether and/or other volatile organic solvents and the resulting solution may either be sprayed on the cured, cased and blended tobacco material or the tobacco material may be dipped into such solution. Under certain circumstances, a solution of the ketone(s) produced according to the process of our invention taken alone or taken further together with other flavoring additives as set forth above, may be applied by means of a suitable applicator such as a brush or roller on the paper or leaf wrapper for the smoking product, or it may be applied to the filter by either spraying, or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the ketone(s) produced according to the process of our invention in excess of the amounts or concentrations above-indicated so that when blended with other tobaccos, the final product will have the percentage within the indicated range.

In accordance with one specific example of our invention, an aged, cured and shredded domestic burley tobacco is sprayed with a 20% ethyl alcohol solution of 5-methyl-3,5-octadiene-2-one mixture of cis and trans isomers in an amount to provide a tobacco composition containing 800 ppm by weight of the 5-methyl-3,5-octadiene-2-one on a dry basis. Thereafter, the alcohol is removed by evaporation and the tobacco is manufactured into cigarettes by the usual techniques. The cigarette when treated as indicated has a desired and pleasing aroma (increased smoke body sensation in the mouth with enhanced tobacco-like notes and pleasant aromatic nuances) which is detectable in the main and side streams when the cigarette is smoked. This aroma is described as having sweet, fruity, Virginia tobacco like notes.

While our invention is particularly useful in the manufacture of smoking tobacco, such as cigarette tobacco, cigar tobacco and pipe tobacco, other tobacco products formed from sheeted tobacco dust or fines may also be used. Likewise, the ketone(s) produced according to the process of our invention can be incorporated with materials such as filter tip materials, seam paste, packaging materials and the like which are used along with tobacco to form a product adapted for smoking. Furthermore, the ketone(s) produced according to the process of our invention can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The following art examples serve to illustrate our invention and the invention is to be considered restricted thereto only as indicated in the appended claims.

All parts and percentages given herein are by weight unless otherwise specified.

EXAMPLE I

PREPARATION OF 3-PENTEN-2-ONE

Into a 2 liter autoclave are place 580 grams (10 moles) acetone, 110 grams (2.5 moles) acetaldehyde, 70 grams (0.86 moles) zinc oxide; and 150 grams (2.5 moles) acetic acid. The autoclave is sealed and the reaction mass is heated at 160°–170° C. for a period of 5 hours. After filtering the catalyst (zinc acetate) the reaction mass is washed with saturated sodium bicarbonate to remove acetic acid. The organic layer is dried over anhydrous sodium sulfate and distilled with 15 grams Primol ® and 1 gram Ionox ® using a 12"×1" Goodloe packed column and yielding 79.3 grams of 3-penten-2-one. During the reaction the autoclave pressure built up to 240 psi.

EXAMPLE II

PREPARATION OF 3-PENTEN-2-ONE USING ZINC ACETATE CATALYST INITIALLY

Into a 2 liter autoclave are placed 220 grams (5 moles) acetaldehyde; 870 grams (15 moles) acetone and 219 grams (1 mole) zinc acetate. The autoclave is sealed and heated at 140° C. for a period of 3 hours, the pressure build up being from 110–130 psig. At the end of the three hour period the autoclave is opened and the zinc acetate catalyst is filtered. The reaction mass is distilled at a vapor temperature of 70° C. and 150 mmHg vacuum giving 181 g of 3-penten-2-one.

EXAMPLE III

PREPARATION OF 3,5-HEPTADIEN-2-ONE

Into a 2 liter autoclave are placed croton aldehyde (247 grams, 85% pure), acetone (580 grams) and zinc acetate dihydrate (186 grams). The reaction mixture is heated at 130°–135° C. for 3.5 hours. After filtering the catalyst the filtrate is washed with 10% salt solution. Distillation giving 124 grams (34% yield) of the product. P.B. 60° C./5 mmHg.

EXAMPLE IV

PREPARATION OF 5-METHYL-3,5-OCTADIEN-2-ONE

Into a 2 liter autoclave are charged 2-methyl-2-pentenal (196 grams), acetone (580 grams) and zinc acetate dihydrate. The reaction mixture is heated at 170°–180° C. for a period of 5 hours. After filtering the catalyst the organic layer is washed with 10% salth solution. Distillation giving 93 grams (34% yield) of the product, B.P. 82°–982° C./7 mmHg.

Figure 2:
FIG. 2 is the NMR spectrum for 5-methyl-3,5-octadien-2-one produced according to Example IV.
Figure 3:
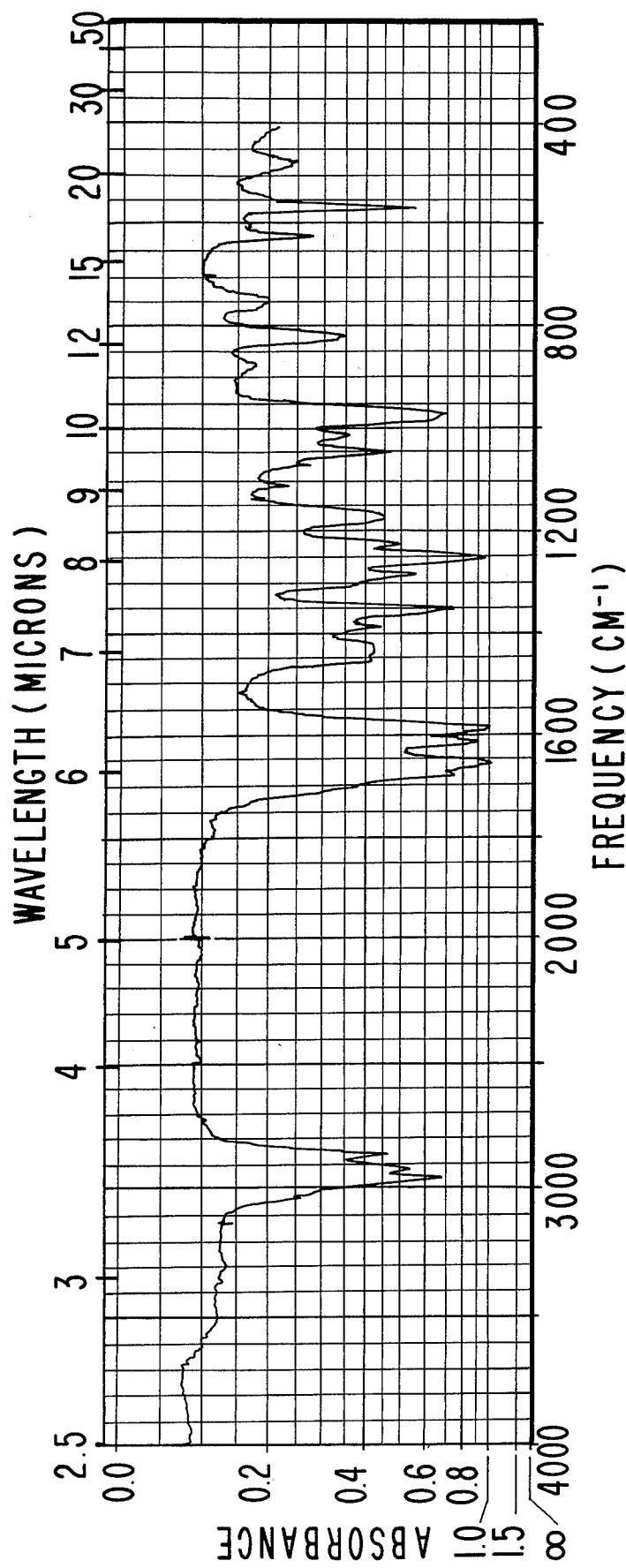
FIG. 3 is the infrared spectrum for 5-methyl-3,5-octadien-2-one produced according to Example IV.

FIG. 1 is the GLC profile for the reaction mixture. FIG. 2 is NMR spectrum for 5-methyl-3,5-octadien-2-one prepared according to the instant example and which fraction 8 consists entirely of. FIG. 3 is the infrared spectrum for fraction 8 of the above mentioned distillation which is essentially 5-methyl-3,5-octadien-2-one.

EXAMPLE V

PREPARATION OF 4-HEXEN-3-ONE

Into a 2 liter autoclave are placed 132 grams (3 moles) of acetaldehyde, 648 grams (9 moles) of methyl ethyl ketone and 132 grams (0.6 moles) of zinc acetate is added. The autoclave is sealed and the reaction mass is heated at 130°–180° C. for a period of 6 hours. The autoclave is then opened and the catalyst is filtered. The filtrate is then distilled after adding thereto 15 grams Primol ® and 1 gram Ionol using a 2" splash column. The fractions collected boiled at 43°–92° C. at 11 mmHg yielding 111 grams (38%). The ratio being hexenone and methyl pentenone is 31:69.

Figure 4:
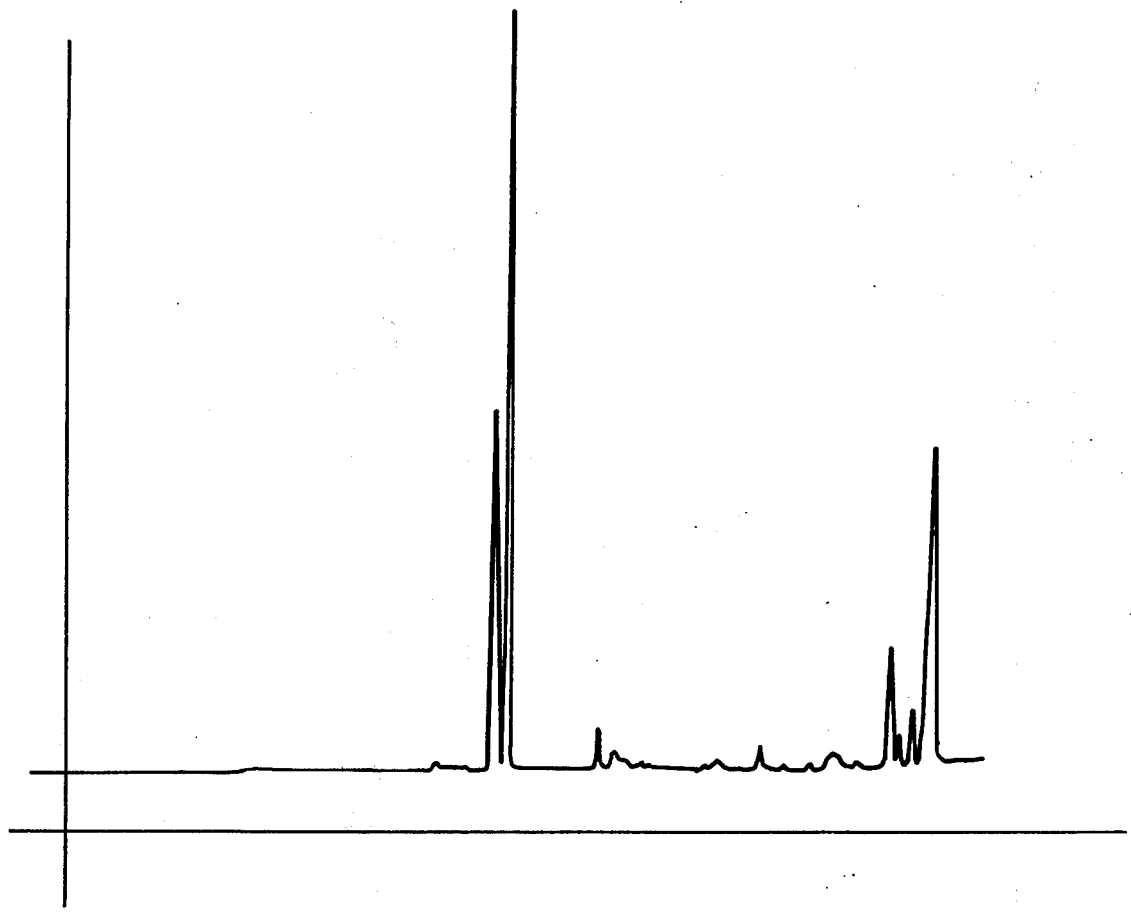
FIG. 4 is the GLC profile for the reaction mixture including 4-hexene-3-one produced according to Example V.

FIG. 4 is the GLC profile of the reaction product of this example.

EXAMPLE VI

PREPARATION OF 6,10-DIMETHYL-3-(OR 4)-9-UNDECADIEN-2-ONE

In a 2 liter autoclave are charged citronellal (154 grams), acetone (174 grams) and zinc acetate dihydrate (44 grams). The reaction mixture is heated at 150° C. for a period of 3 hours. After filtering off the catalyst the organic layer is washed with 200 ml of 10% salt solution. Distillation giving 101 grams of crude product, B.P. 109°–112° C./2.5 mmHg. Redistillation with 4.5' Vigreux column yielding 23 grams (12% of yield) of the product, B.P. 109°–112° C./2.5 mmHg.

EXAMPLE VII

PREPARATION OF MIXTURE OF 3,6,10-TRIMETHYL-3(AND 4)-9-UNDECADIEN-2-ONE AND 7,11-DIMETHYL-4(AND 5)-10-DODECADIEN-3-ONE

Into a 2 liter autoclave are charged citronellal (154 grams), methyl ethyl ketone (360 grams) and zinc acetate dihydrate (44 grams). The reaction mixture is heated at 160° C. for a period of 8 hours. After filtering off the catalyst, the organic layer is washed with 200 ml of 10% salt solution. Distillation giving 142 grams of crude product having B.P. 55°–125° C./2 mmHg. Redistillation using a 4.5' Vigreux column yielding 87 grams (45% yield) of product having B.P. 75°–104° C./2 mmHg.

Figure 5:
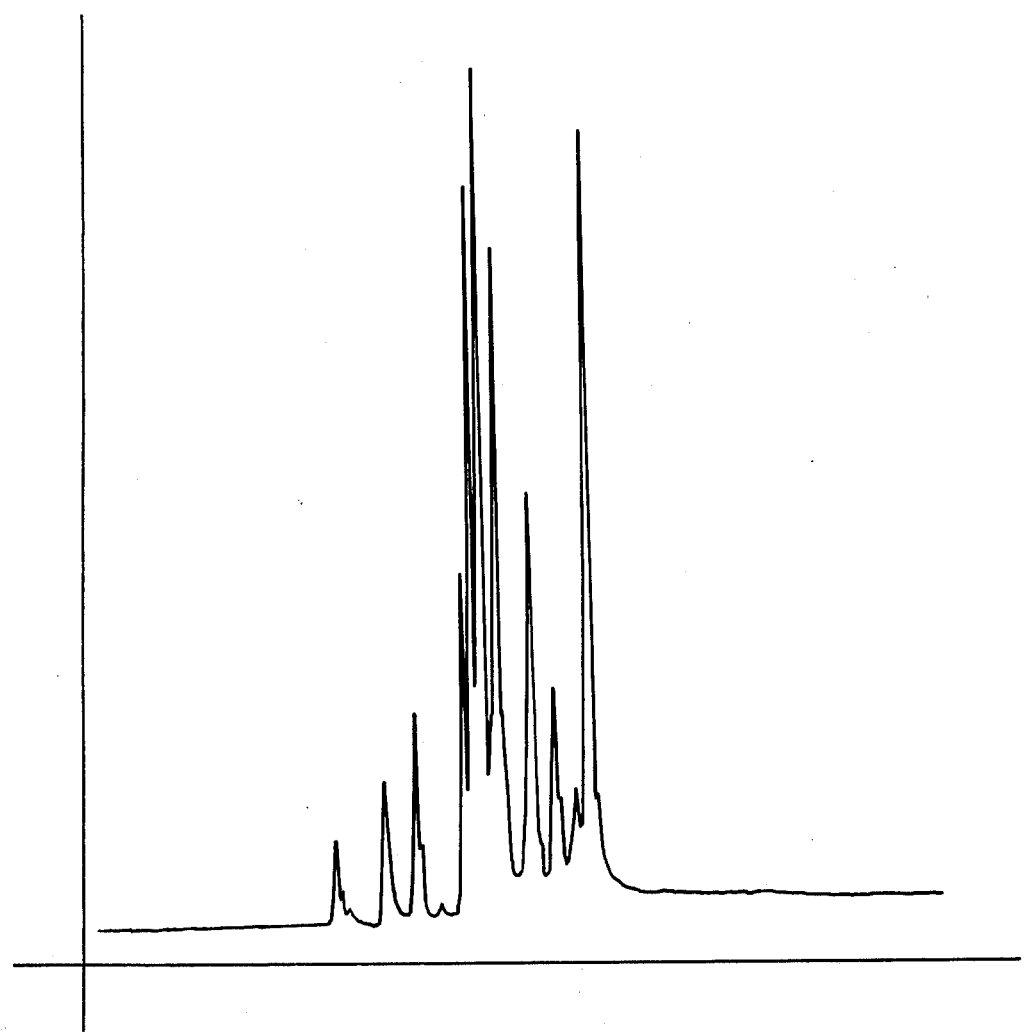
FIG. 5 is the GLC profile for the reaction mixture containing the mixture of 3,6,10-trimethyl-3(and 4),9-undecadiene-2-one and 7,11-dimethyl-4(and 5),10-dodecadien-3-one produced according to Example VII.

FIG. 5 is the GLC profile for the reaction product prepared according to the instant example.

EXAMPLE VIII

PREPARATION OF 2,8,12-TRIMETHYL-5,7,11-TRIDECATRIEN-4-ONE

Into a 2 liter autoclave are charged citral (152 grams), methyl isobutyl ketone (500 grams) and zinc acetate dihydrate (38 grams). The reaction mixture is heated at 160° C. for a period of 12 hours. After filtering the catalyst the organic layer is washed with 10% salt solution. Distillation yielding 76 grams (32% yield) of the product, B.P. 126°–141° C./1 mmHg.

EXAMPLE IX

PREPARATION OF 4-(4-METHYL-3-CYCLOHEXENE-1-YL)-3-BUTEN-2-ONE AND 4-METHYL-3-CYCLOHEX-1-YLIDENE-2-BUTANONE

Into a 2 liter autoclave are charged 4-methyl-4-cyclohexen-1-aldehyde (248 grams), acetone (340 grams) and zinc acetate dihydrate (88 grams). The reaction mixture was heated at 180° C. The reaction mixture was heated at 180° C. for a period of 7 hours. After removing the catalyst the organic layer is washed with 10% salt solution. Distillation giving 191 grams of crude product, B.P. 70°–155° C./3 mmHg Redistillation using a 4.5' Vigreux column yielding 154 grams (47% yield) of the product having B.P. 93°–104° C./2 mmHg.

Figure 6:
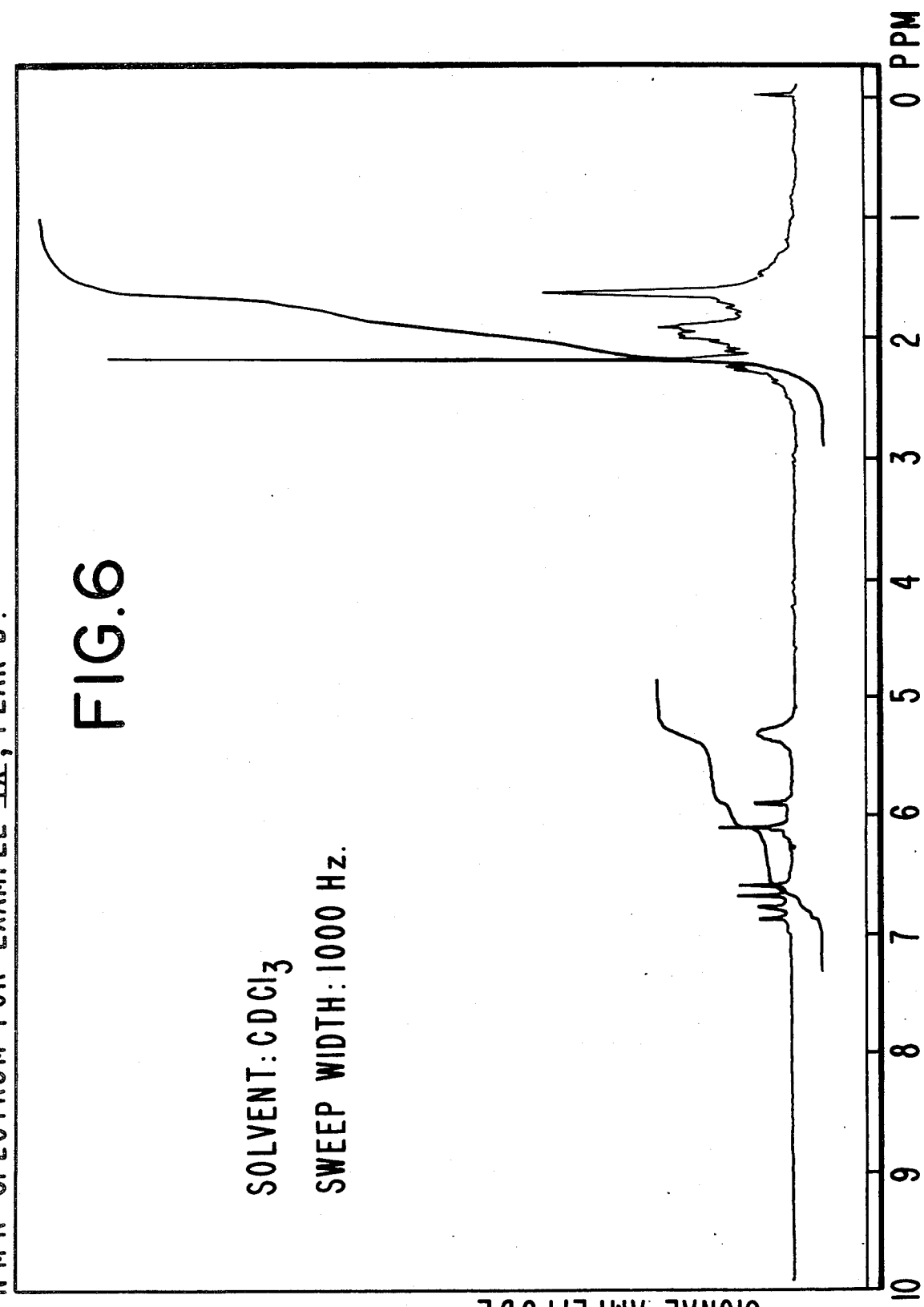
FIG. 6 is the NMR spectrum for 4-(4-methyl-3-cyclohexene-1-yl)-trans-3-buten-2-one produced according to Example IX.
Figure 7:
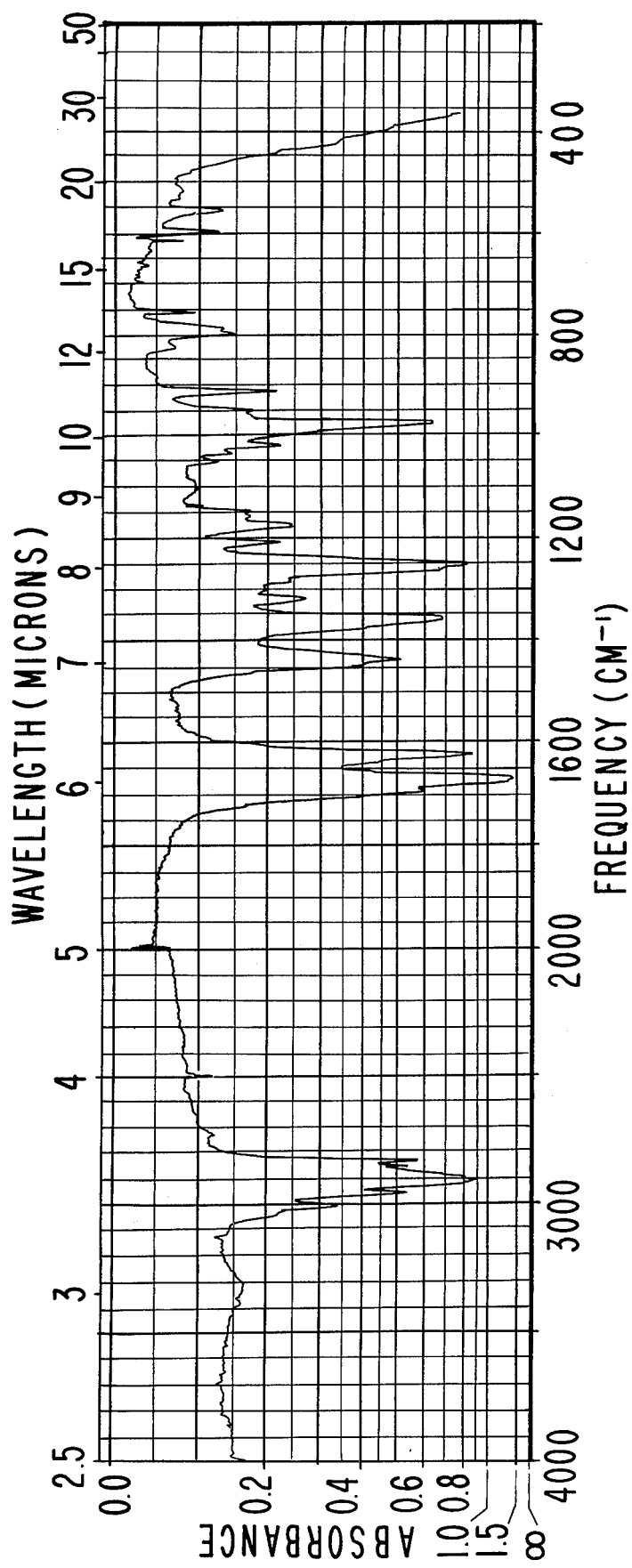
FIG. 7 is the IR spectrum for 4-(4-methyl-3-cyclohexene-1-yl)-trans-3-buten-2-one.
Figure 8:
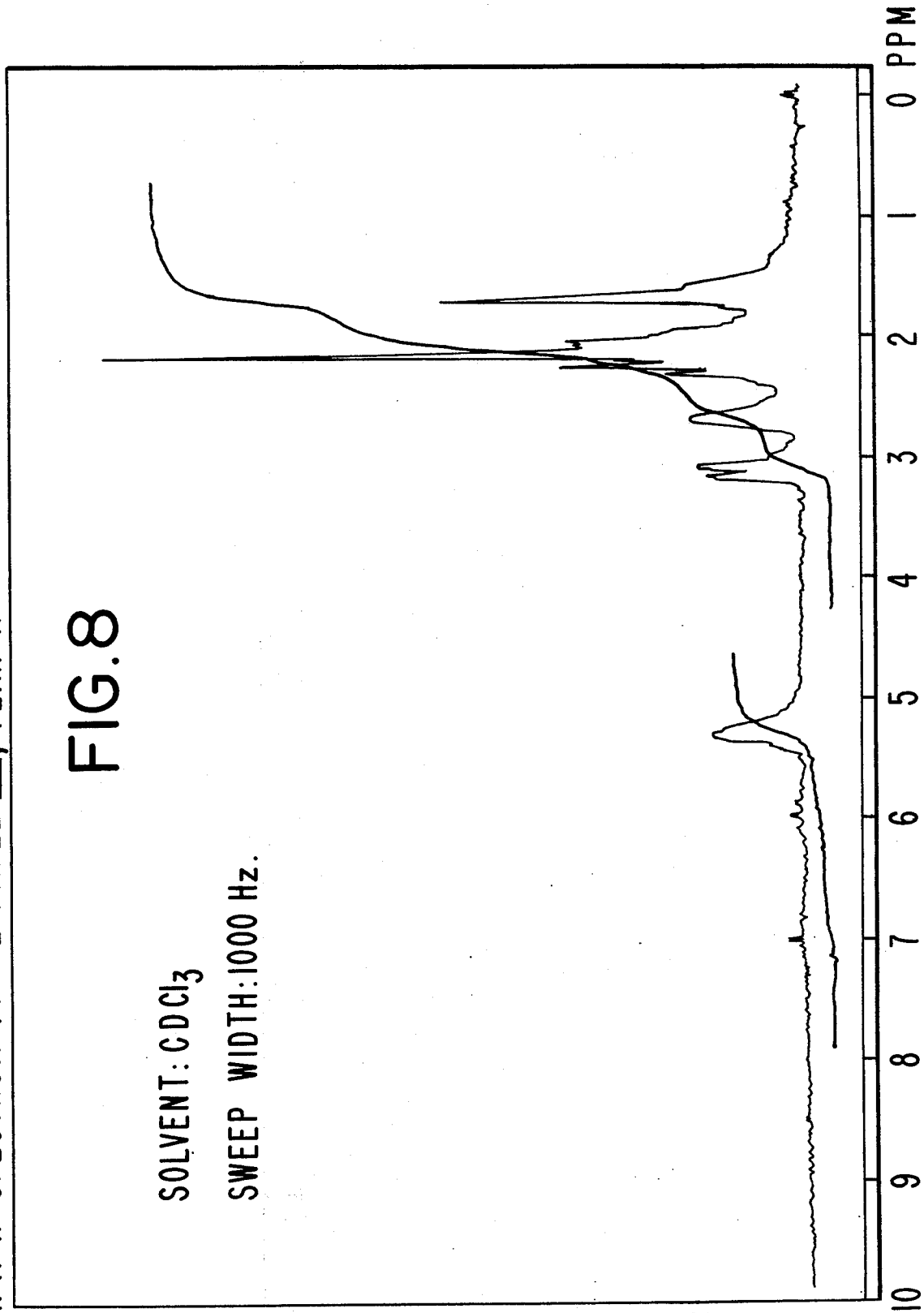
FIG. 8 is the NMR spectrum for 4-(4-methyl-3-cyclohexene-1-yl)-cis-3-buten-2-one.
Figure 9:
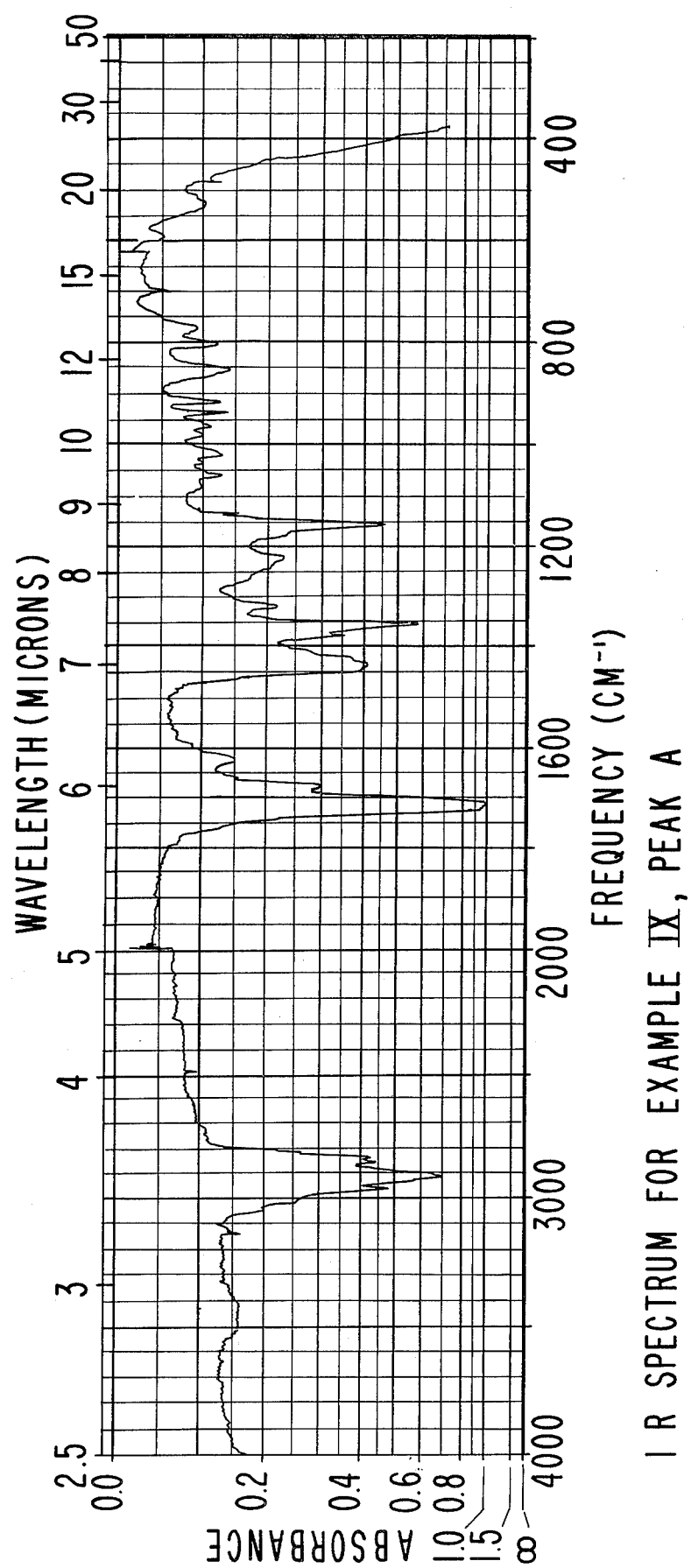
FIG. 9 is the IR spectrum for 4-(4-methyl-3-cyclohexene-1-yl)-cis-3-buten-2-one produced according to Example IX.

FIG. 6 is the NMR spectrum for the trans isomer of 4-(4-methyl-3-cyclohexene-1-yl)-3-buten-2-one. FIG. 7 is the IR spectrum for the trans isomer of 4-(4-methyl-3-cyclohexene-1-yl)-3-buten-2-one. FIG. 8 is the NMR spectrum for the cis isomer of 4-(4-methyl-3-cyclohexene-1-yl)-3-buten-2-one. FIG. 9 is the IR spectrum for the cis isomer of 4-(4-methyl-3-cyclohexene-1-yl)-3-buten-2-one.

EXAMPLE X

PREPARATION OF A MIXTURE OF 3-METHYL-4-(4-METHYL-3-CYCLOHEXEN-1-YL)3-BUTEN-2-ONE AND 1-(4-METHYL-3-CYCLOHEXEN-1-YL)-1-PENTEN-3-ONE

Into a 2 liter autoclave are charged 4-methyl-3-cyclohexen-1-aldehyde (124 grams), methyl ethyl ketone (360 grams) and zinc acetate dihydrate (44 grams). The reaction mixture is heated at 150° C. for a period of 10 hours. After filtering the catalyst, the organic layer is washed with 10% salt solution. Distillation yielding 111 grams of crude product, B.P. 97°–138° C./3 mmHg. Redistillation with 4.5' Vigreux column yielded 101 grams (57% yield) of the product, B.P. 119°–125° C./3 mmHg.

Figure 10:
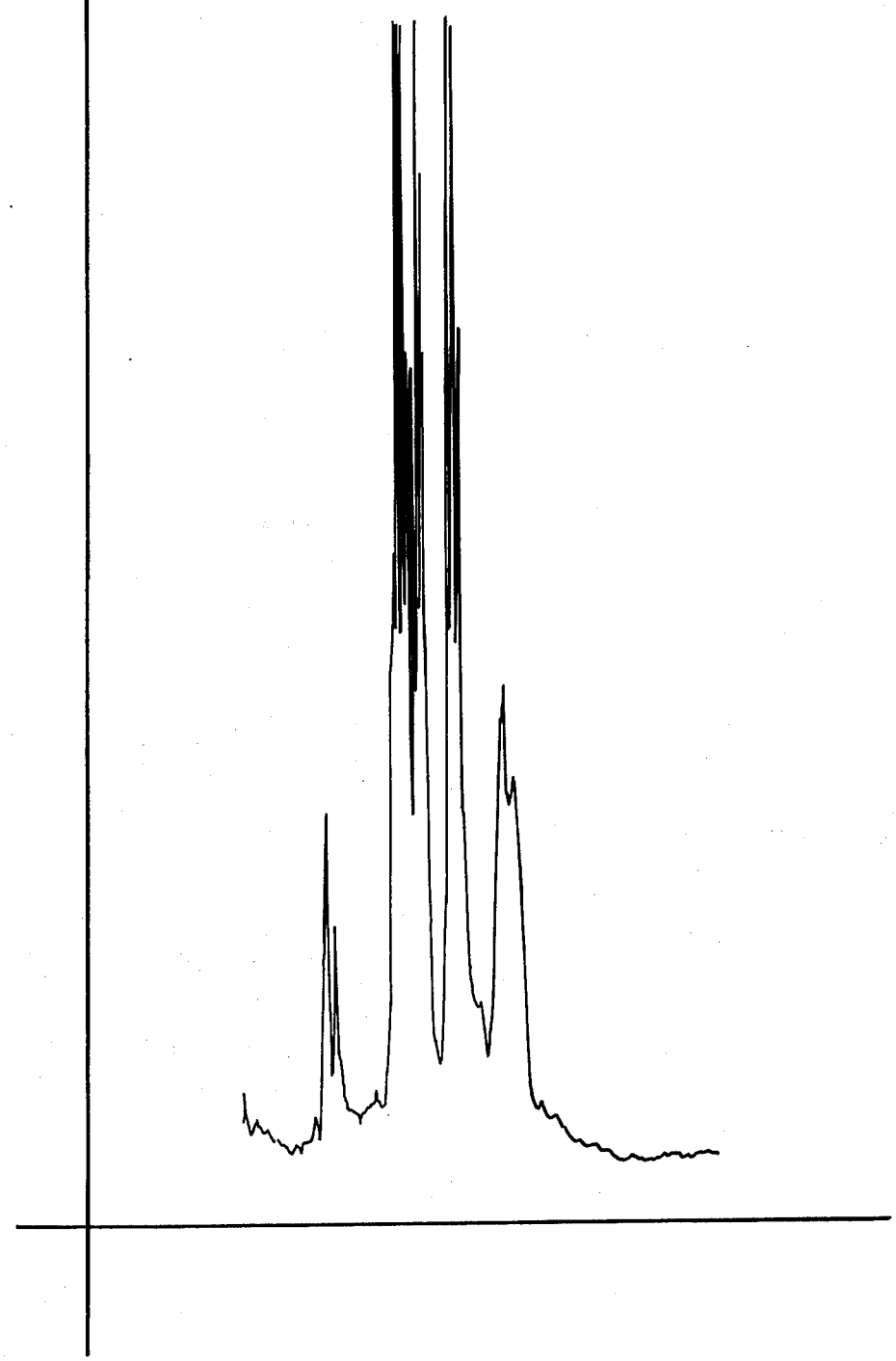
FIG. 10 is the GLC profile for the reaction product of Example X which contains a mixture of 3-methyl-4-(4-methyl-3-cyclohexene-1-yl)-3-butene-2-one and 1-(4-methyl-3-cyclohexene-1-yl)-1-pentene-3-one.

FIG. 10 is the GLC profile for the reaction product produced according to this example.

EXAMPLE XI

PREPARATION OF 5-PHENYL-3(AND 4)-HEXEN-2-ONE

Into a 2 liter autoclave are charged hydratropic aldehyde (268 grams), acetone (580 grams) and zinc acetate dihydrate (88 grams). The reaction mixture is heated at 150°–165° C. for a period of 10 hours. After filtering the catalyst the filtrate was washed with 10% salt solution. Distillation yielding 187 grams (54% yield) of the product, B.P. 100°–122° C./1.4–2.8 mmHg.

EXAMPLE XII

PREPARATION OF 3-METHYL-5-PHENYL-3(AND 4)-HEXEN-2-ONE AND 6-PHENYL-4(AND 5)-HEPTEN-3-ONE

Into a 2 liter autoclave are placed hydratropic aldehyde (268 grams), methyl ethyl ketone (720 grams) and zinc acetate dihydrate (88 grams). The reaction mixture is heated at 150°–170° C. for a period of 10 hours. After filtering the catalyst the filtrate is washed with 10% salt solution. Distillation yielding 221 grams (59% yield) of the product.

Figures 11, 12:
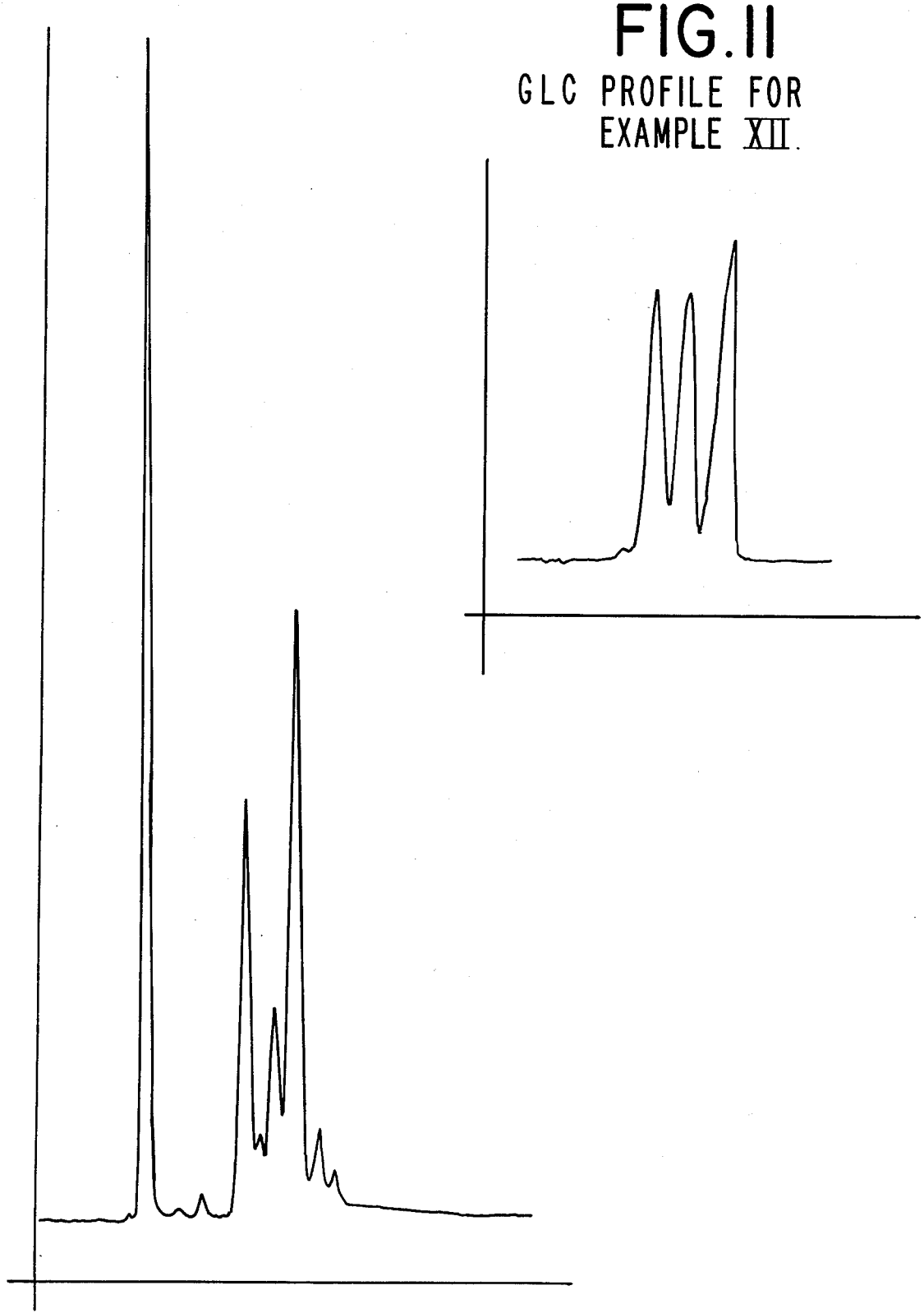
FIG. 11 is the GLC profile for the reaction product of Example XII which contains 3-methyl-5-phenyl- 3(and 4) hexene-2-one and 6-phenyl-4(and 5)-hepten-3-one.
FIG. 12 is the GLC profile for the reaction product of Example XIII which contains a mixture of 3-methyl-3(and 4)-hexen-2-one and 4(and 5)-hepten-3-one.

FIG. 11 is the GLC profile for the reaction product produced according to the instant example.

EXAMPLE XIII

PREPARATION OF A MIXTURE OF 3-METHYL-3(AND 4)-HEXEN-2-ONE AND 4-(AND 5)-HEPTEN-3-ONE

Into a 2 liter autoclave are charged propionaldehyde (87 grams), methyl ethyl ketone (540 grams) and zinc acetate dihydrate (66 grams). The reaction mixture is heated at 190° C. for a period of 12 hours. After filtering the catalyst the filtrate is washed with 10% salt solution. Distillation yielding 59 grams (35% yield) of the product. B.P. 72°–100° C./30 mmHg.

FIG. 12 is the GLC profile for the reaction product produced according to the instant example.

EXAMPLE XIV

PREPARATION OF A MIXTURE OF 3-METHYL-5-(2,6,6,-TRIMETHYL-1(AND 2)-CYCLOHEXEN-1-YL)-3(AND 4)-PENTEN-2-ONE AND 6-(2,6,6-TRIMETHYL-1(AND 2)-CYCLOHEXEN-1-YL)-4(AND 5)-HEXEN-3-ONE

Into a 2 liter autoclave are charged 2,6,6-trimethyl-1(and 2)-cyclohexene acetaldehyde (75 grams), methyl ethyl ketone (325 grams) and zinc acetate dihydrate (20 grams). The reaction mixture is heated at 190° C. for 8 hours. After filtering the catalyst the organic layer is washed with 10% salt solution. Distillation yielding 56 grams (56% yield) of the product. B.P. 116°–121° C./1.3 mmHg.

Figure 13:
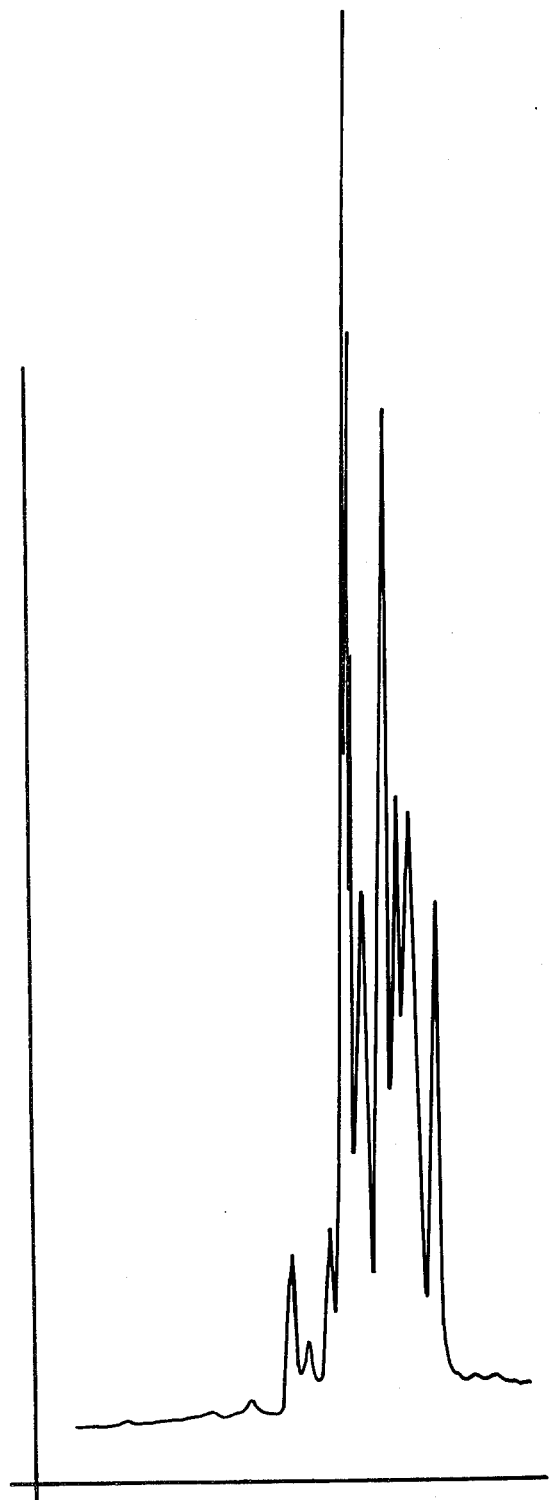
FIG. 13 is the GLC profile for the reaction product of Example XIV which contains a mixture of 3-methyl-5-(2,6,6-trimethyl-1 (and 2)-cyclohexene-1-yl)-3(and 4)-penten 2-one and 6-(2,6,6-trimethyl-1(and 2)-cyclohexene-1-yl)-4(and 5)-hexene-3-one.

FIG. 13 is the GLC profile for the reaction product produced according to this example.

FIG. 14 is the NMR spectrum for fraction 4 produced according to this example which contains substantially all 5-(2,6,6-trimethyl-1(and 2)-cyclohexen-1-yl)-3-methyl-3-penten-2-one.

FIG. 15 is the IR spectrum for fraction 4 produced according to this example which contains substantially all 5-(2,6,6-trimethyl-1(and 2)-cyclohexen-1-yl)-3-methyl-3-penten-2-one.

EXAMPLE XV

PREPARATION OF 3-PENTEN-2-ONE

Into a 1 gallon autoclave are charged zinc acetate dihydrate (350 grams), acetaldehyde (350 grams) and acetone (1400 grams). The reaction is carried out at 140° C. for a period of three hours during which time the pressure increases to 75–110 psig. After the autoclave is cooled to room temperature the reaction mixture is filtered and zinc acetate dihydrate is washed with acetone (200 grams). The collected zinc acetate catalyst is again charged into the autoclave. To this is added 350 grams of acetaldehyde and 1400 grams of acetone and the reaction is repeated under the same conditions. This procedure is repeated a total of 4 times and the analysis of the reaction mixture is as follows:

| Batch | Reaction Mixture wt. (g) | 3-Penten-3-one wt % | Rinse Wt. (g) |
|---|---|---|---|
| #1 | 1212 | 16.6 | 222 |
| #2 | 1535 | 17.5 | 219 |
| #3 | 1271 | 18.0 | 320 |
| #4 | 1380 | 18.8 | 216 |
| Total | 5398 | | 977 |

The analysis is carried out using GLC (conditions: SE-30 column programmed at 80°–200° C. at 4° C. per minute).

Distillation (no reflux) of the combined mixture (6375 grams) using a 12"×1½" procelain saddle packed column with 20 grams of Primol ® and 1 grams of Ionox ® under atmospheric pressure yields the following fractions:

| Fr. No. | Vapor Temp. | Liq. Temp. | Weight | Product |
|---|---|---|---|---|
| 1 | 50–70 | 64–83 | 3834 | 130 |
| 2 | 70–73 | 83–86 | 182 | 26 |
| 3 | 73–78 | 86–90 | 184 | 45 |
| 4 | 78–80 | 90–92 | 122 | 47 |
| 5 | 80–91 | 92–95 | 171 | 91 |
| 6 | 91–118 | 95–200 | 867 | 737 |

The weight of residue is 807 grams.

The isolated yield is 867 grams (purity: 85% as mixture of cis and trans 3-penten-2-one; 5% 4-penten-2-one; 5% mesityl oxide and 5% water.

The following table sets forth runs carried out using the same procedure as above except with variation of catalyst, the reaction conditions (time and temperature) and acetaldehyde; acetone mole ratio.

| Run | Acetaldehyde Reactant (mole) | Acetone Reactant (mole) | Catalyst (mole) | Reaction Condition | Yield (%) |
|---|---|---|---|---|---|
| 1 | 2.7 | 12.4 | ZnO(1.0) | 140°–150° C., 3 hr. | 13 |
| 2 | 2.7 | 12.4 | ZnO(1.0)+AcOH(0.1) | 135°–140° C., 3 hr. | 14 |
| 3 | 5.0 | 10.0 | ZnO(1.0)+AcOH(2.0) | 160°–170° C., 5 hr. | 23 |
| 4 | 2.5 | 10.0 | ZnO(0.86)+AcOH(2.5) | 160°–170° C., 5 hr. | 38 |

-continued

| Run | Acetaldehyde Reactant (mole) | Acetone Reactant (mole) | Catalyst (mole) | Reaction Condition | Yield (%) |
|---|---|---|---|---|---|
| 5 | 5.0 | 15.0 | Zn(OAc)$_2$ . 2H$_2$O(1.0) | 135°–140° C., 3 hr. | 43 |
| 6 | 5.0 | 15.0 | Zn(OAc)$_2$ . 2H$_2$O(1.0) | 180°–190° C., 3.5 Hr. | 43 |
| 7 | 5.0 | 15.0 | Zn(OAc)$_2$ . 2H$_2$O(1.0) | 100° C., 5 hr. | 8 |
| 8 | 5.0 | 15.0 | Zn(OAc)$_2$ . 2H$_2$O(0.5) | 140° C., 3 hr. | 34 |
| 9 | 5.0 | 15.0 | Zn(OAc)$_2$ . 2H$_2$O(0.33) | 140° C., 3 hr. | 23 |
| 10 | 8.0 | 24.0 | Zn(OAc)$_2$ . 2H$_2$O(1.6) | 140° C., 3 hr. | 40 |
| 11 | 3.0 | 12.0 | Zn(OAc)$_2$ . 2H$_2$O(0.6) | 140° C., 3 hr. | 40 |
| 12 | 3.0 | 15.0 | Zn(OAc)$_2$ . 2H$_2$O(1.0) | 140° C., 3 hr. | 51 |
| 13 | 2.0 | 6.0 | Zn(OAc)$_2$(0.4) | 130°–140° C., 3 hr. | 10 |
| 14 | 2.0 | 6.0 | Zn(OAc)$_2$(0.4) | 140° C., 6 hr. | 31 |
| 15 | 2.0 | 6.0 | Zn(OAc)$_2$ . 2H$_2$O+B$_2$O$_3$(0.8) | 120°–150° C., 3 hr. | 18 |
| 16 | 5.0 | 10.0 | B(OH)$_2$(2.0)+B$_2$O$_3$(1.7) | 150° C., 5 hr. | 22 |

Figure 16:
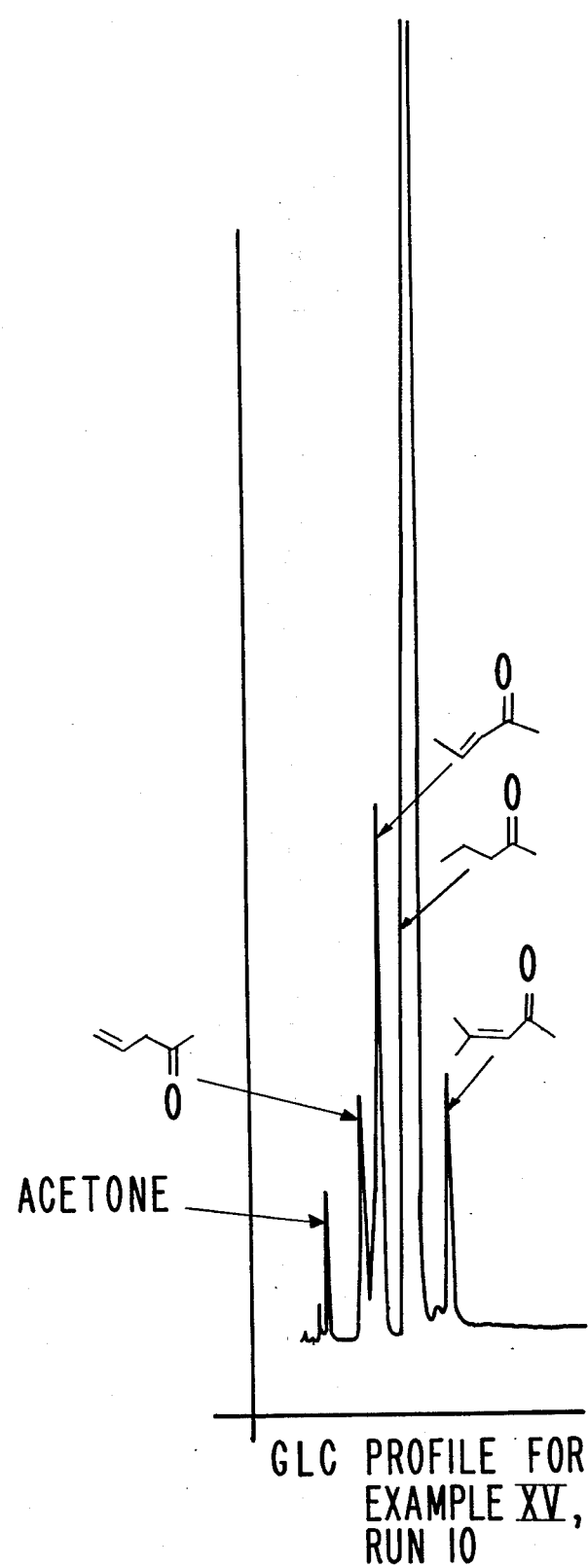
FIG. 16 is the GLC profile profile for the reaction product of Run 10 of Example XV containing 3-penten-2-one.
Figure 17:
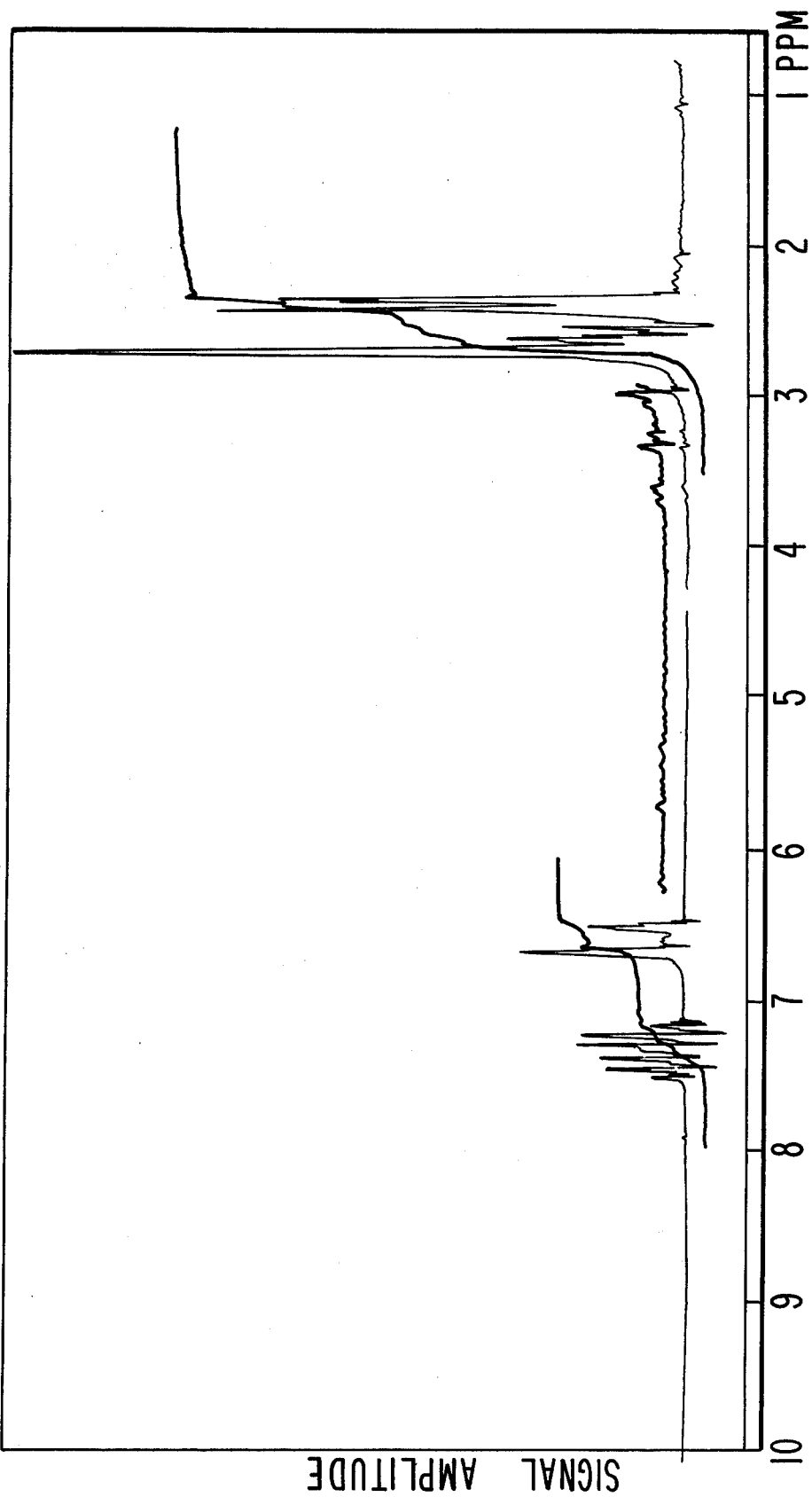
FIG. 17 is the NMR spectrum for 3-penten-2-one produced according to Run 10 of Example XV.
Figure 18:
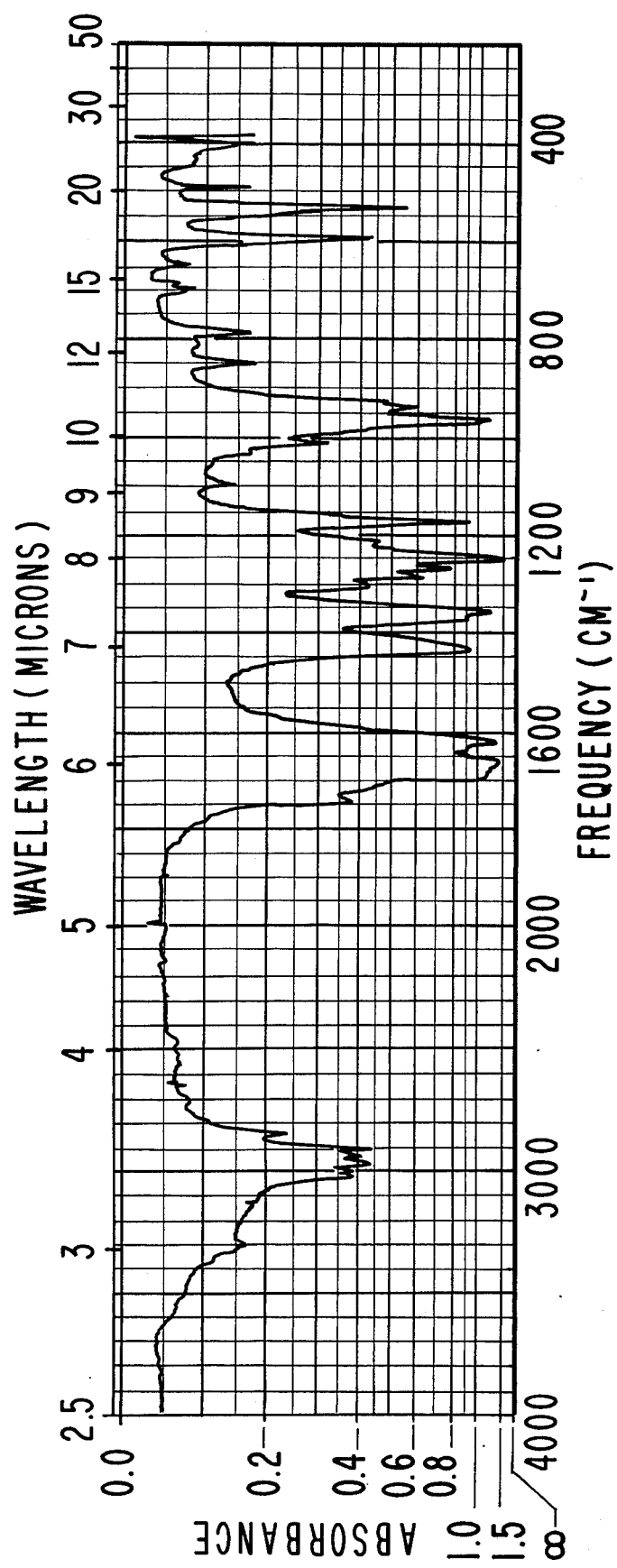
FIG. 18 is the infrared spectrum for the 3-penten-2-one produced according to Example XV, Run 10.

FIG. 16 is the GLC profile for the reaction product produced according to Run 10. FIG. 17 is the NMR spectrum for the 3-penten-2-one produced according to Run 10 (fraction 18), FIG. 18 is the IR spectrum for the 3-penten-2-one produced according to Run 10 (fraction 18).

EXAMPLE XVI

Concentrated liquid detergents with green, herbaceous and melony notes (which detergents are produced from the Lisine salt of n-dodecyl benzene sulfonic acid as more specifically described in U.S. Pat. No. 3,948,818, issued on Apr. 6, 1976) are prepared containing the 4(4-methyl-3-cyclohexen-1-yl)-3-cis and trans buten-2-ones prepared according to Example IX. They are prepared by adding an homogeneously admixing the appropriate quantity of mixture of 4(4-methyl-3-cyclohexen-1-yl)-3-cis and trans buten-2-ones in the liquid detergent. The detergents all possess green, herbaceous, and melony aromas with woody nuances, the intensity increasing with greater concentrations of mixture of 4(4-methyl-3-cyclohexen-1-yl)-3-buten-2-ones.

EXAMPLE XVII

Preparation of a cologne and handkerchief perfume. The cis-4-(4-methyl-3-cyclohexen-1-yl)-3-cis-buten-2-one prepared according to Example IX is incorporated into a cologne at concentrations of 1.5%, 2.0%, 2.5%, 3.0%, 3.5%, 4.0% and 4.5% in 85% aqueous food grade ethanol; and into handerchief perfumes at concentrations of 15%, 20%, 25% and 30% (in 95% aqueous ethanol). Distinct and definite grain, herbaceous and melony aromas are imparted to the cologne and to the handkerchief perfume at each of the levels indicated.

EXAMPLE XVIII

OTTO OF ROSE FORMULATION

The following mixture is prepared:

| Ingredients | Parts by Weight |
|---|---|
| Phenyl acetic acid | 5 |
| Hydroxycitronellal | 10 |
| Geraniol | 125 |
| Citronellol | 150 |
| Phenyl ethyl alcohol | 50 |
| Phenyl ethyl acetate | 4 |
| Ethyl phenyl acetate | 5 |
| Citronellyl formate | 20 |
| Geranyl acetate | 25 |
| Linalool | 15 |
| Terpineol | 10 |
| Eugenol | 3 |

-continued

| Ingredients | Parts by Weight |
|---|---|
| Phenyl acetaldehyde dimethyl acetal | 5 |
| Benzyl acetate | 3 |
| Guaiacwood Oil | 5 |
| trans 4(4-methyl-3-cyclohexen-1-yl)-3-trans-buten-2-one prepared according to Example IX | 10 |

The 4(4-methyl-3-cyclohexen-1-yl)3-trans-buten-2-one prepared according to Example IX imparts a green, herbaceous and spicy aroma so characteristic of Rose Otto to this formulation.

EXAMPLE XIX

RASPBERRY FLAVOR FORMULATION

The following basic raspberry flavor formulation is produced:

| Ingredient | Parts by Weight |
|---|---|
| Vanillin | 2.0 |
| Maltol | 5.0 |
| Parahydroxybenzylacetone | 5.0 |
| Alpha-ionone (10% in propylene glycol | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |
| | 1000.0 |

With a mixture of cis and trans 4(4-methyl-3-cyclohexene-1-yl)-3-buten-2-one prepared according to Example IX is added to half of the above formulation at the rate of 0.3%. The formulation with the said butenone is compared with the formulation said butenone at the rates of 0.01%, 0.02% and 0.05% (100, 200 and 500 ppm) in water and evaluated by a bench panel.

A flavor containing the said butenone is found to have a substantially more pleasant and raspberry aroma. It is the unanomous opinion of the bench panel that the chemical, the mixture of cis and trans 4(4-methyl-3-cyclohexen-1-yl)-3-buten-2-one contributes to a very natural and fresh aroma and taste as found in the full ripe raspberries. Accordingly, the flavor with the addition of the mixture produced according to Example IX is considered as substantially better than the flavor without the material produced according to Example IX.

EXAMPLE XX

TOBACCO FORMULATION

A tobacco mixture is produced by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1000 ppm of mixture produced according to Example IX of cis and trans 4-(4-methyl-3-cyclohexen-1-yl)-3-buten-2-one. The control cigarettes not containing said butenone produced according to Example IX and the experimental cigarettes which contain the mixture of said butenones produced according to Example IX are evaluated by paired comparison and the results are as follows:

The experimental cigarettes are found to have more body in tobacco smoke flavor and a fuller body sensation. The tobacco-like notes are enhanced and the flavor of the tobacco on smoking is more aromatic with floral, hay-tealike, sweet and fruity aroma and taste nuances.

The tobacco smoke flavor of the experimental cigarettes, prior to smoking, has floral, sweet and fruity notes. All cigarettes are evaluated for smoke flavor with a 20 mm cellulose acetate filter.

EXAMPLE XXI

PREPARATION OF A DETERGENT COMPOSITION

A total of 100 grams of a detergent powder (a non-ionic detergent powder containing a proteolytic enzyme prepared according to Example I of Canadian Pat. No. 985,190, issued on Mar. 9, 1976) is mixed with 0.15 grams of 5-methyl-3,5-octadien-2-one (fraction 5) prepared according to Example IV until a substantially homogeneous composition is obtained. This composition has an excellent walnut, melony, lactonic character with floral undertones.

EXAMPLE XXII

CINNAMON FLAVOR FORMULATION

A cinnamon-like-butter formulation is prepared by admixing the following ingredients:

| Ingredients | Parts by Weight |
| --- | --- |
| Butter | 10 |
| Sucrose | 2 |
| 5-methyl-3,5-octadien-2-one | 100 |

The 5-methyl-3,5-octadien-2-one (fraction 5) produced according to Example IV enhances the sweet, nutty, woody and cinnamon characteristics of the cinnamon flavor and causes it to be more natural.

EXAMPLE XXIII

PERFUMED LIQUID DETERGENTS

Concentrated liquid detergents with rich, sour berry aromas are prepared containing 0.10%, 0.15%, 0.20% of the mixture produced according to Example IVX containing 3-methyl-5-(2,6,6-trimethyl-1(and 2)-cyclohexen-1-yl)-3(and 4)-penten-2-ones prepared according to Example XIV. They are prepared by adding and homogeneously admixing said pentenones with the appropriate quantity of liquid detergent. The liquid detergents are all produced using anionic detergents containing a 50:50 mixture of sodium lauroyl sarcosinate and potassium N-methyl lauroyl tauride. The detergents all possess pleasant fragrances which have excellent woody, ionone-like aromas with sour berry undertones.

What is claimed is:

1. The process of reacting an aldehyde with a ketone using a catalyst selected from the group consisting of zinc acetate and zinc acetate dihydrate whereby an alpha, beta unsaturated ketone is formed according to the reaction sequence:

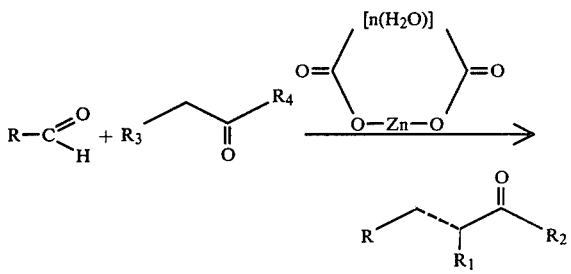

wherein the dashed line represents a cis or trans carbon-carbon double bond and n=0 or 2, said reaction being carried out in the liquid phase at an elevated temperature sufficient to produce the desired product wherein R is lower alkyl having from 1 up to about 5 carbon atoms; alkenyl having from 3 up to 12 carbon atoms; alkadienyl having from 8 up to 12 carbon atoms; alkyl cycloalkenyl alkyl having from 8 up to 10 carbon atoms; alkyl alkenyl having from 7 up to 9 carbon atoms; and aryl alkyl having 7 or 8 carbon atoms; wherein $R_1$ and $R_3$ are each the same and each represents hydrogen or lower alkyl having from 1 up to 5 carbon atoms; and wherein $R_2$ and $R_4$ are each the same and each represents lower alkyl having from 1 up to 5 carbon atoms.

2. The process of reacting an unsaturated aldehyde with a ketone in the presence of a catalyst selected from the group consisting of zinc acetate and zinc acetate dihydrate thereby forming an unsaturated dienone according to the reaction scheme:

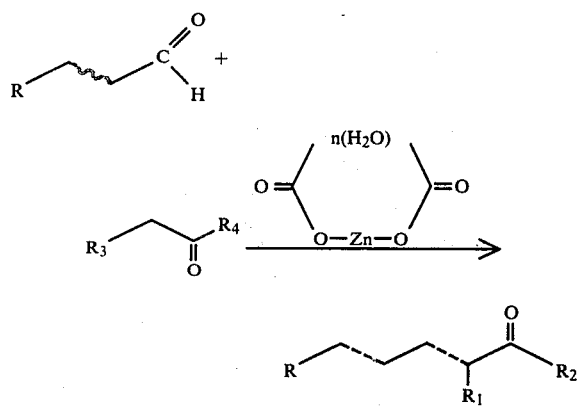

wherein the wavy line and each of the dashed lines represent cis or trans carbon-carbon double bonds and n=0 or 2; and wherein R is lower alkyl having from one up to about five carbon atoms; alkenyl having from three up to twelve atoms; alkadienyl having from eight up to twelve carbon atoms; alkyl cycloalkyl alkyl having from eight up to ten carbon atoms; alkyl alkenyl having from seven up to nine carbon atoms and aralkyl having from seven to eight carbon atoms; wherein $R_1$ and $R_3$ are each the same and each represents hydrogen or lower alkyl having from one up to five carbon atoms; and wherein $R_2$ and $R_4$ are each the same and each represents lower alkyl having one up to five carbon atoms; the reaction being carried out in the liquid phase and at an elevated temperature sufficient to produce the desired product.

3. The process of claim 1 wherein the mole ratio of catalyst:ketone reaction varies from about 0.05:1 up to about 1:1; and the reaction temperature being from about 100° C. up to about 250° C.

4. The process of claim 1 wherein the mole ratio of catalyst:ketone reaction varies from about 0.05:1 up to about 1:1, the mole ratio of ketone:aldehyde reactants varies from about 1:1 up to about 10:1; and the reaction temperature varying from about 100° C. up to about 250° C.

* * * * *